US011666650B2

(12) United States Patent
Zhao et al.

(10) Patent No.: US 11,666,650 B2
(45) Date of Patent: Jun. 6, 2023

(54) IMMUNE COMPOSITION COMPRISING RESPIRATORY SYNCYTIAL VIRUS (RSV) G POLYPEPTIDE

(71) Applicant: ADVACCINE (SUZHOU) BIOPHARMACEUTICALS CO. LTD., Suzhou (CN)

(72) Inventors: Gan Zhao, Suzhou (CN); Aihua Dong, Suzhou (CN); Zhonghuai He, Suzhou (CN); Qingling Yu, Suzhou (CN); Cheng Sui, Suzhou (CN)

(73) Assignee: ADVACCINE (SUZHOU) BIOPHARMACEUTICALS CO. LTD., Suzhou (CN)

( * ) Notice: Subject to any disclaimer, the term of this patent is extended or adjusted under 35 U.S.C. 154(b) by 0 days.

(21) Appl. No.: 16/985,736

(22) Filed: Aug. 5, 2020

(65) Prior Publication Data

US 2021/0113683 A1   Apr. 22, 2021

Related U.S. Application Data

(60) Provisional application No. 62/885,370, filed on Aug. 12, 2019.

(51) Int. Cl.
*C12N 7/00* (2006.01)
*A61K 39/155* (2006.01)
*A61P 31/14* (2006.01)
*A61K 9/08* (2006.01)
*A61K 38/13* (2006.01)

(52) U.S. Cl.
CPC ............. *A61K 39/155* (2013.01); *A61K 9/08* (2013.01); *A61K 38/13* (2013.01); *A61P 31/14* (2018.01); *C12N 2760/18522* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

2016/0250256 A1\* 9/2016 Klingemann ........ C12N 5/0646
424/85.2

FOREIGN PATENT DOCUMENTS

| CN | 1271389 A | 10/2000 |
|---|---|---|
| CN | 101264323 A | 9/2008 |
| CN | 103239734 A | 8/2013 |
| CN | 104870007 A | 8/2015 |
| CN | 105983095 A | * 10/2016 |

(Continued)

OTHER PUBLICATIONS

EPO English translation of CN105983095A (Year: 2022).*

(Continued)

*Primary Examiner* — M Franco G Salvoza
(74) *Attorney, Agent, or Firm* — McDermott Will & Emery LLP

(57) ABSTRACT

Immune compositions comprising (i) a respiratory syncytial virus (RSV) G polypeptide, which may be a modified G polypeptide relative to the wild-type counterpart, or a nucleic acid encoding such, and (ii) a solvent and one or more immune regulators, wherein the immune regulator(s) is dissolvable in the solvent. Also provided herein are methods for eliciting anti-RSV immune responses using the immune compositions disclosed herein and methods for producing the immune compositions.

12 Claims, 24 Drawing Sheets

Specification includes a Sequence Listing.

(56) References Cited

FOREIGN PATENT DOCUMENTS

| CN | 105983095 A | 10/2016 | | |
|----|-------------|---------|---|---|
| WO | WO-2015084838 A1 | * | 6/2015 | ........... A61K 39/155 |
| WO | WO-2016205641 A2 | * | 12/2016 | ............. A61K 39/12 |

OTHER PUBLICATIONS

Cmte for Veterinary Medicinal Products, "Polyethylene Glycol Stearates and Polyethylene Glycol 15 Hydroxystearate," European Agency for the Evaluation of Medicinal Products, Veterinary Medicines and Inspections found at https://www.ema.europa.eu/en/documents/mrl-report/polyethylene-glycol-stearates (Year: 2003).*

Li et al., A Recombinant G Protein Plus Cyclosporine A-Based Respiratory Syncytial Virus Vaccine Elicits Humoral and Regulatory T Cell Responses against Infection without Vaccine-Enhanced Disease. J Immunol. Feb. 15, 2016;196(4):1721-31. doi: 10.4049/jimmunol.1502103. Epub Jan. 20, 2016.

[No Author Listed], GenBank Accession No. CAA34937.1 G protein [Human orthopneumovirus]. Jun. 24, 1992. 1 page.

* cited by examiner

G + CsA in Kolliphor

G + CsA in propylene

A : Treg (G+CSA) +Spleen cells (G)
B : Treg (G+CSA) +Spleen cells (PBS)
C : Treg (PBS) +Spleen cells (G)
B : Treg (PBS) +Spleen cells (PBS)

SEQUENCE LISTING

<160> NUMBER OF SEQ ID NOS: 9

<210> SEQ ID NO 1
<211> LENGTH: 232
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Truncated form of a wild-type RSV G protein

<400> SEQUENCE: 1

His Lys Val Thr Leu Thr Thr Ala Ile Ile Gln Asp Ala Thr Ser Gln
1               5                   10                  15

Ile Lys Asn Thr Thr Pro Thr Tyr Leu Thr Gln Asp Pro Gln Leu Gly
            20                  25                  30

Ile Ser Phe Ser Asn Leu Ser Glu Ile Thr Ser Gln Thr Thr Thr Ile
        35                  40                  45

Leu Ala Ser Thr Thr Pro Gly Val Lys Ser Asn Leu Gln Pro Thr Thr
    50                  55                  60

Val Lys Thr Lys Asn Thr Thr Thr Thr Gln Thr Gln Pro Ser Lys Pro
65                  70                  75                  80

Thr Thr Lys Gln Arg Gln Asn Lys Pro Pro Asn Lys Pro Asn Asn Asp
                85                  90                  95

Phe His Phe Glu Val Phe Asn Phe Val Pro Cys Ser Ile Cys Ser Asn
            100                 105                 110

Asn Pro Thr Cys Trp Ala Ile Cys Lys Arg Ile Pro Asn Lys Lys Pro
        115                 120                 125

Gly Lys Lys Thr Thr Thr Lys Pro Thr Lys Lys Pro Thr Phe Lys Thr
    130                 135                 140

Thr Lys Lys Asp Leu Lys Pro Gln Thr Thr Lys Pro Lys Glu Val Pro
145                 150                 155                 160

Thr Thr Lys Pro Thr Glu Glu Pro Thr Ile Asn Thr Thr Lys Thr Asn
                165                 170                 175

Ile Thr Thr Thr Leu Leu Thr Asn Asn Thr Thr Gly Asn Pro Lys Leu
            180                 185                 190

Thr Ser Gln Met Glu Thr Phe His Ser Thr Ser Ser Glu Gly Asn Leu
        195                 200                 205

Ser Pro Ser Gln Val Ser Thr Thr Ser Glu His Pro Ser Gln Pro Ser
    210                 215                 220

Ser Pro Pro Asn Thr Thr Arg Gln
225                 230

<210> SEQ ID NO 2
<211> LENGTH: 232
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Modified RSV G protein 1(2)

<400> SEQUENCE: 2

His Lys Val Thr Leu Thr Thr Ala Ile Ile Gln Asp Ala Thr Ser Gln
1               5                   10                  15

Ile Lys Asn Thr Thr Pro Thr Tyr Leu Thr Gln Asp Pro Gln Leu Gly
            20                  25                  30

```
Ile Ser Phe Ser Asn Leu Ser Glu Ile Thr Ser Gln Thr Thr Thr Ile
        35                  40                  45

Leu Ala Ser Thr Thr Pro Gly Val Lys Ser Asn Leu Gln Pro Thr Thr
 50                  55                  60

Val Lys Thr Lys Asn Thr Thr Thr Thr Gln Thr Gln Pro Ser Lys Pro
 65                  70                  75                  80

Thr Thr Lys Gln Arg Gln Asn Lys Pro Pro Asn Lys Pro Asn Asn Asp
                 85                  90                  95

Ser His Ser Glu Val Ser Asn Ser Val Pro Ser Ser Ile Cys Ser Asn
                100                 105                 110

Asn Pro Thr Cys Trp Ala Ile Ser Lys Arg Ile Pro Asn Lys Lys Pro
            115                 120                 125

Gly Lys Lys Thr Thr Thr Lys Pro Thr Lys Lys Pro Thr Phe Lys Thr
130                 135                 140

Thr Lys Lys Asp Leu Lys Pro Gln Thr Thr Lys Pro Lys Glu Val Pro
145                 150                 155                 160

Thr Thr Lys Pro Thr Glu Glu Pro Thr Ile Asn Thr Thr Lys Thr Asn
                165                 170                 175

Ile Thr Thr Thr Leu Leu Thr Asn Asn Thr Thr Gly Asn Pro Lys Leu
                180                 185                 190

Thr Ser Gln Met Glu Thr Phe His Ser Thr Ser Ser Glu Gly Asn Leu
                195                 200                 205

Ser Pro Ser Gln Val Ser Thr Thr Ser Glu His Pro Ser Gln Pro Ser
            210                 215                 220

Ser Pro Pro Asn Thr Thr Arg Gln
225                 230

<210> SEQ ID NO 3
<211> LENGTH: 232
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Modified RSV G protein 3

<400> SEQUENCE: 3

His Lys Val Thr Leu Thr Thr Ala Ile Ile Gln Asp Ala Thr Ser Gln
 1               5                  10                  15

Ile Lys Asn Thr Thr Pro Thr Tyr Leu Thr Gln Asp Pro Gln Leu Gly
                 20                  25                  30

Ile Ser Phe Ser Asn Leu Ser Glu Ile Thr Ser Gln Thr Thr Thr Ile
        35                  40                  45

Leu Ala Ser Thr Thr Pro Gly Val Lys Ser Asn Leu Gln Pro Thr Thr
 50                  55                  60

Val Lys Thr Lys Asn Thr Thr Thr Thr Gln Thr Gln Pro Ser Lys Pro
 65                  70                  75                  80

Thr Thr Lys Gln Arg Gln Asn Lys Pro Lys Lys Pro Lys Asp Asp
                 85                  90                  95

Tyr His Phe Glu Val Phe Asn Phe Val Pro Cys Ser Ile Cys Gly Asn
                100                 105                 110

Asn Gln Leu Cys Lys Ser Ile Cys Lys Thr Ile Pro Ser Asn Lys Pro
            115                 120                 125

Lys Lys Lys Thr Thr Thr Lys Pro Thr Lys Lys Pro Thr Phe Lys Thr
130                 135                 140
```

-continued

```
Thr Lys Lys Asp Leu Lys Pro Gln Thr Thr Lys Pro Lys Glu Val Pro
145                 150                 155                 160

Thr Thr Lys Pro Thr Glu Glu Pro Thr Ile Asn Thr Thr Lys Thr Asn
            165                 170                 175

Ile Thr Thr Thr Leu Leu Thr Asn Asn Thr Thr Gly Asn Pro Lys Leu
        180                 185                 190

Thr Ser Gln Met Glu Thr Phe His Ser Thr Ser Ser Glu Gly Asn Leu
    195                 200                 205

Ser Pro Ser Gln Val Ser Thr Thr Ser Glu His Pro Ser Gln Pro Ser
    210                 215                 220

Ser Pro Pro Asn Thr Thr Arg Gln
225                 230
```

<210> SEQ ID NO 4
<211> LENGTH: 232
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Modified RSV G protein 4

<400> SEQUENCE: 4

```
His Lys Val Thr Pro Thr Thr Ala Ile Ile Gln Asp Ala Thr Ser Gln
1               5                   10                  15

Ile Lys Asn Thr Thr Pro Thr Tyr Leu Thr Gln Asn Pro Gln Leu Gly
            20                  25                  30

Ile Ser Pro Ser Asn Pro Ser Glu Ile Thr Ser Gln Ile Thr Thr Ile
        35                  40                  45

Leu Ala Ser Thr Thr Pro Gly Val Lys Ser Thr Leu Gln Ser Thr Thr
    50                  55                  60

Val Lys Thr Lys Asn Thr Thr Thr Thr Gln Thr Gln Pro Ser Lys Pro
65                  70                  75                  80

Thr Thr Lys Gln Arg Gln Asn Lys Pro Pro Ser Lys Pro Asn Asn Asp
                85                  90                  95

Phe His Phe Glu Val Phe Asn Phe Val Pro Cys Ser Ile Cys Ser Asn
            100                 105                 110

Asn Pro Thr Cys Trp Ala Ile Cys Lys Arg Ile Pro Asn Lys Lys Pro
        115                 120                 125

Gly Lys Lys Thr Thr Thr Lys Pro Thr Lys Lys Pro Thr Leu Lys Thr
    130                 135                 140

Thr Lys Lys Asp Pro Lys Pro Gln Thr Thr Lys Ser Lys Glu Val Pro
145                 150                 155                 160

Thr Thr Lys Pro Thr Glu Glu Pro Thr Ile Asn Thr Thr Lys Thr Asn
                165                 170                 175

Ile Ile Thr Thr Leu Leu Thr Ser Asn Thr Thr Gly Asn Pro Glu Leu
            180                 185                 190

Thr Ser Gln Met Glu Thr Phe His Ser Ser Ser Ser Glu Gly Asn Pro
        195                 200                 205

Ser Pro Ser Gln Val Ser Thr Thr Ser Glu Tyr Pro Ser Gln Pro Ser
    210                 215                 220

Ser Pro Pro Asn Thr Pro Arg Gln
225                 230
```

<210> SEQ ID NO 5
<211> LENGTH: 696

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Modified RSV G protein 1(2)

<400> SEQUENCE: 5
cataaggtga ccctgactac tgctatcatc caggacgcaa ctagccaaat caaaaacacc    60
acgccgacct acctgactca ggatcctcag ctgggtatca gcttcagcaa cctgtctgag   120
atcacttctc agactacgac gatcctggcc tctaccactc caggtgtaaa atccaacctg   180
cagccaacca ccgtgaaaac caaaaatacc actaccaccc agacccagcc gtctaaacca   240
actacgaaac agcgtcagaa caaaccgcct aacaaaccaa caacgactc ccactccgag    300
gtctctaact ccgttccgtc ctctatctgt tctaacaacc cgacttgctg ggcgatttct   360
aaacgcattc cgaacaagaa acctggtaaa aagaccacca cgaaaccgac gaaaaagccg   420
accttcaaaa ccaccaagaa agatctgaaa ccgcagacca ctaaaccgaa agaagttccg   480
acgaccaaac cgaccgaaga accgaccatt aataccacca aaaccaacat taccaccact   540
ctgctgacga caacaccac tggcaacccg aaactgacct cccagatgga aacctttcac   600
agcacctcca gcgaaggcaa tctgtccccg tcccaggtta gcaccactag cgaacacccg   660
agccaaccgt cttctccgcc gaacactact cgtcaa                              696

<210> SEQ ID NO 6
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Modified RSV G protein 1(2)

<400> SEQUENCE: 6
cacaaagtca cactaacaac tgcaatcata caagatgcaa caagccagat caagaacaca    60
accccaacat acctcactca ggatcctcag cttggaatca gcttctccaa tctgtctgaa   120
attacatcac aaaccaccac catactagct tcaacaacac caggagtcaa gtcaaacctg   180
caacccacaa cagtcaagac taaaaacaca acaacaaccc aaacacaacc cagcaagccc   240
actacaaaac aacgccaaaa caaaccacca acaaaccca ataatgatag tcacagtgaa    300
gtgagtaaca gtgtacccag tagcatatgc agcaacaatc aacctgctg ggctatcagt    360
aaaagaatac caaacaaaaa accaggaaag aaaccacca ccaagcctac aaaaaaacca    420
accttcaaga caaccaaaaa agatctcaaa cctcaaacca ctaaaccaaa ggaagtaccc   480
accaccaagc ccacagaaga gccaaccatc aacaccacca aaacaaacat cacaactaca   540
ctgctcacca caacaccac aggaaatcca aaactcacaa gtcaaatgga aaccttccac   600
tcaacctcct ccgaaggcaa tctaagccct tctcaagtct ccaacatc cgagcaccca   660
tcacaaccct catctccacc caacacaaca cgccagtag                           699

<210> SEQ ID NO 7
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
```

<221> NAME/KEY: misc_feature
<223> OTHER INFORMATION: Modified RSV G protein 3

<400> SEQUENCE: 7

| | | | | | |
|---|---|---|---|---|---|
| cacaaagtca | cactaacaac | tgcaatcata | caagatgcaa | caagccagat | caagaacaca | 60 |
| accccaacat | acctcactca | ggatcctcag | cttggaatca | gcttctccaa | tctgtctgaa | 120 |
| attacatcac | aaaccaccac | catactagct | tcaacaacac | caggagtcaa | gtcaaacctg | 180 |
| caacccacaa | cagtcaagac | taaaaacaca | acaacaaccc | aaacacaacc | cagcaagccc | 240 |
| actacaaaac | aacgccaaaa | caaaccacca | acaaaccca | ataatgattt | tcacttcgaa | 300 |
| gtgtttaact | ttgtaccctg | cagcatatgc | agcaacaatc | caacctgctg | ggctatctgc | 360 |
| aaaagaatac | caaacaaaaa | accaggaaag | aaaaccacca | ccaagcctac | aaaaaaacca | 420 |
| accttcaaga | caaccaaaaa | agatctcaaa | cctcaaacca | ctaaaccaaa | ggaagtaccc | 480 |
| accaccaagc | ccacagaaga | gccaaccatc | aacaccacca | aaacaaacat | cacaactaca | 540 |
| ctgctcacca | caacaccac | aggaaatcca | aaactcacaa | gtcaaatgga | aaccttccac | 600 |
| tcaacctcct | ccgaaggcaa | tctaagccct | tctcaagtct | ccacaacatc | cgagcaccca | 660 |
| tcacaaccct | catctccacc | caacacaaca | cgccagtag | | | 699 |

<210> SEQ ID NO 8
<211> LENGTH: 696
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Modified RSV G protein 4

<400> SEQUENCE: 8

| | | | | | |
|---|---|---|---|---|---|
| cataaagtaa | ccccgaccac | cgctatcatc | caggacgcta | ccagccagat | caaaaacact | 60 |
| acgcctacct | atctgactca | gaacccgcaa | ctgggcatct | ccccgtccaa | tccgtctgaa | 120 |
| attacctccc | agatcactac | catcctggca | tccactactc | cgggtgtgaa | atctaccctg | 180 |
| cagtccacta | ccgtaaaaac | gaaaacacc | accactaccc | agactcagcc | ttccaaacct | 240 |
| actacgaaac | agcgtcagaa | caaaccgccg | agcaaaccga | caacgactt | ccactttgaa | 300 |
| gttttcaact | tcgtcccatg | cagcatttgt | agcaacaatc | cgacctgctg | ggcaatttgc | 360 |
| aaacgcatcc | caaacaaaaa | gccgggcaaa | aagacgacca | ctaaaccaac | caagaaacct | 420 |
| accctgaaaa | ctaccaaaaa | agacccgaaa | ccgcagacca | ccaaatctaa | gaagttccg | 480 |
| acgaccaaac | cgaccgagga | accgacgatc | aacaccacga | aaacgaacat | catcaccacc | 540 |
| ctgctgacct | ctaacactac | cggtaatccg | gagctgacta | gccagatgga | aacctttcac | 600 |
| agcacttctt | ctgaaggtaa | cccatctccg | agccaggtgt | ccaccacttc | tgaatacccg | 660 |
| agccaaccgt | cctccccgcc | taatacgccg | cgtcaa | | | 696 |

<210> SEQ ID NO 9
<211> LENGTH: 298
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Wild-type RSV G protein

<400> SEQUENCE: 9

-continued

```
Met Ser Lys Asn Lys Asp Gln Arg Thr Ala Lys Thr Leu Glu Lys Thr
1               5                   10                  15

Trp Asp Thr Leu Asn Tyr Leu Leu Phe Ile Ser Ser Gly Leu Tyr Lys
            20                  25                  30

Leu Asn Leu Lys Ser Ile Ala Gln Ile Thr Leu Ser Ile Leu Ala Met
            35                  40                  45

Ile Ile Ser Thr Ser Leu Ile Ile Thr Ala Ile Ile Phe Ile Ala Ser
50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
            85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
            115                 120                 125

Thr Thr Val Lys Thr Lys Asn Thr Thr Thr Thr Gln Thr Gln Pro Ser
            130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
            195                 200                 205

Lys Thr Thr Lys Lys Asp Leu Lys Pro Gln Thr Thr Lys Pro Lys Glu
210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
            245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
            275                 280                 285

Pro Ser Ser Pro Pro Asn Thr Thr Arg Gln
            290                 295
```

IMMUNE COMPOSITION COMPRISING RESPIRATORY SYNCYTIAL VIRUS (RSV) G POLYPEPTIDE

RELATED APPLICATIONS

This application claims priority under 35 U.S.C § 119(e) to U.S. Provisional Application No. 62/885,370, filed Aug. 12, 2019, which is incorporated by reference herein in its entirety.

BACKGROUND OF THE INVENTION

Respiratory Syncytial Virus (RSV) is a single-chain negative-sense RNA virus of Paramyxoviridae, which mainly causes acute lower respiratory tract infections (ALRIs) in infants and older populations. It is also one of the main causes of pneumonia in children under 5 years old. Epidemiological data show that about 60% of infants are infected with the virus during the RSV epidemic season; almost 100% of children under 5 years of age have been infected with RSV. Among RSV infection cases, about 18% are severe cases and about 20% need hospitalization, whereas 15% are outpatient cases. Among infected individuals, about 30,000 infants and young children worldwide die from RSV infection each year. About ⅓ of the children under the age of five are treated with RSV infection each year, and 60% of RSV outpatients are children aged 2-5.

Despite the fact that RSV being a serious health threat to infants and young children, there is no yet approved vaccine available worldwide after over 50 years of research. There are many types of RSV vaccine candidates being tested in various clinic trials. One example is RSV inactivated vaccine, which can generate antibodies against RSV proteins, but the level of neutralizing antibodies is low, and the severe inflammatory cells including Th2 cells and granulocytes being infiltrated into the lungs of the subjects. As the result, few subjects participated in this clinic trials progressed the severe lung disease and even death when re-exposure to the virus. Another example is subunit vaccine, which uses F and G proteins, the major capsid proteins of RSV with neutralizing epitopes, to elicit certain levels of neutralizing antibodies, leading to inhibit the replication of RSV in animal models. However, these subunit recombinant proteins could activate T cell responses, which could result in Th2 response and enhanced respiratory disease (ERD), raising safety concerns. Further, live attenuated vaccines have been developed to stimulate local and systemic immune responses by intranasal administration. While most of attenuated vaccines derived from other type of viruses are effective and safe for infants who are older than 6 months, this type of RSV vaccines raises safety concerns in infants under 6 months via induction of a moderate inflammatory response in the lung.

SUMMARY OF THE INVENTION

The present disclosure is based, at least in part, on the development of immune compositions comprising RSV G protein (wild-type, fragment thereof, or modified) and one or more immune regulators (e.g., CsA), and optionally a suitable solvent (e.g., polyethylene glycol (15)-hydroxystearate, for example, Kolliphor® HS 15) capable of forming an aqueous solution of the immune regulator(s), wherein the aqueous solution, containing the immune regulator(s), can dissolve the RSV G protein. Such immune compositions have shown a number of advantageous features, for example, high activity in inducing immune responses against RSV and little or no hemolytic effect, little or no local irritation/inflammation.

Accordingly, one aspect of the present disclosure provides an immune composition, comprising (i) a modified respiratory syncytial virus (RSV) G protein or a nucleic acid encoding the modified RSV G protein, and (ii) one or more immune regulators and optionally a solvent, which can dissolve the immune regulator(s). The modified RSV protein may lack a transmembrane domain as compared with the wild-type counterpart. Further, the modified RSV G protein may comprise an amino acid sequence at least 90% identical to SEQ ID NO:1. In some instances, the modified RSV G protein comprises one or more mutations at one or more positions corresponding to L5, D28, F35, L38, T45, N59, P62, N91, N94, N95, F97, F99, F102, F104, C107, 5111, P114, T115, W117, A118, C120, R122, N125, G129, F142, L149, P156, T178, N184, K191, L208, H219, and/or T230 in SEQ ID NO:1.

In some embodiments, the one or more mutations in the modified RSV G protein can be amino acid substitutions of L5P, D28N, F35P, L38P, T45I, N59T, P62S, N91K, N91S, N94K, N95D, F97S, F97Y, F99S, F102S, F104S, C107S, S111G, P114Q, T115L, W117K, A118S, C120S, R122T, N125S, G129K, F142L, L149P, P156S, T1781, N184S, K191E, L208P, H219Y, and/or T230P. For example, a modified RSV G protein may comprise one or more of: (a) C97S, F99S, F102S, F104S, C107S, and/or C120S; (b) N91K, N94K, N95D, F97Y, S111G, P114Q, T115L, W117K, A118S,R122T, N125S, and/or G129K; or (c) L5P, D28N, F35P, L38P, T45I, N59T, P62S, N91S, F142L, L149P, P156S, T1781, N184S, K191E, L208P, H219Y, and/or T230P. In specific examples, the modified RSV G protein comprises or consists of the amino acid sequence of SEQ ID NO:1, SEQ ID NO:2, SEQ ID NO:3, or SEQ ID NO:4.

In some embodiments, the immune composition disclosed herein may comprise the modified RSV G protein, e.g., those described herein. Alternatively, the immune composition may comprise a nucleic acid encoding any of the modified RSV G proteins disclosed herein. In some instances, the nucleic acid may comprise a nucleotide sequence at least 80% identical to any one of SEQ ID NOs.: 5-8. In particularly examples, the nucleic acid may comprise the nucleotide sequence of any one of SEQ ID NOs:5-8.

In some aspects, the present disclosure provides an immune composition, comprising (a) a respiratory syncytial virus (RSV) G protein or an immunogenic fragment thereof, or a nucleic acid encoding such, (b) a solvent and one or more immune regulators, which is dissolvable in the solvent. The RSV G protein can be a wild-type protein, an immunogenic fragment thereof, or a modified RSV G protein such as those described herein.

In any of the immune compositions disclosed herein, the immune regulator(s) comprises a cyclosporine compound, dexamethasone, FK506, rapamycin, or a combination thereof. In some examples, the immune regulator(s) is a cyclosporine compound, which may be cyclosporine A in some instances. In some embodiments, the immune regulator(s) such as a cyclosporine compound (e.g., cyclosporine A) and the RSV G protein (e.g., any of the modified RSV G proteins disclosed herein) may be at a ratio of 10:1 to 1:10 by weight in the immune composition.

The immune compositions may further comprise a solvent for dissolving the immune regulator(s). In some instances, the solvent may comprise a non-ionic surfactant, a cyclodextrin, a lecithin, or a combination thereof. Exemplary non-ionic surfactants include polyethylene glycol (15)-hydroxystearate, polysorbate 80, polysortabe 20, poloxamer 188, a castor oil (e.g., polyoxyethylene (35) castor oil (EL-35), or polyoxyethylene (40) castor oil (EL-40)), a hydrogenated castor oil (e.g., polyoxyethylene (35) hydrogenated castor oil (RH-35), and polyoxyethylene (40) hydrogenated castor oil (RH-40)), and a polyoxyethylene-polyoxypropylene block copolymer. Exemplary cyclodextrin is hydroxypropyl-β-cyclodextrin. In specific examples, the immune composition disclosed herein may comprise polyethylene glycol (15)-hydroxystearate and cyclosporine A. In some examples, the immune composition is a dosage form comprising about 10-50 μg of the RSV G protein (e.g., any of those modified ones disclosed herein) and about 10-50 μg of cyclosporine A. Any of the immune compositions may further comprise additional immune regulator(s) or adjuvant(s).

In another aspect, provided herein is a method for enhancing immune responses against a respiratory syncytial virus (RSV), the method comprising administering to a subject in need thereof an effective amount of any immune compositions disclosed herein. In some embodiments, the subject is a human subject having, suspected of having, or at risk for RSV infection. Such a subject may be an infant. Alternatively, such a subject may be an elderly.

The immune composition may be administered to the subject intramuscularly or subcutaneously. In some embodiments, the effective amount of the immune composition may contain about 0.1 μg to 500 μg the RSV G protein. In some examples, the effective amount of the immune composition may contain about 10 μg to about 50 μg the RSV G protein such as a modified one as those disclosed herein.

Any of the methods disclosed herein may further comprise, prior to the administering step, mixing a first solution comprising the RSV G protein and a second solution comprising the one or more immune regulator (e.g., cyclosporine A), which is dissolved in the non-ionic surfactant (e.g., polyethylene glycol (15)-hydroxystearate) to form the immune composition.

Also within the scope of the present disclosure are immune compositions as disclosed herein for use in eliciting anti-RSV immune responses in a subject, as well as use of any of the RSV G polypeptides, nucleic acids encoding such, and compositions comprising the RSV G polypeptide or the encoding nucleic acid for manufacturing a medicament for use in the intended therapy as also disclosed herein.

Further, the present disclosure provides an aqueous cyclosporine formulation, comprising a cyclosporine compound and a solvent, which can be polyethylene glycol (15)-hydroxystearate, polysorbate 80, polysortabe 20, poloxamer 188, a castor oil (e.g., polyoxyethylene (35) castor oil (EL-35), and polyoxyethylene (40) castor oil (EL-40)), a hydrogenated castor oil (e.g., polyoxyethylene (35) hydrogenated castor oil (RH-35), and polyoxyethylene (40) hydrogenated castor oil (RH-40)), hydroxypropyl-β-cyclodextrin, lecithin, a polyoxyethylene-polyoxypropylene block copolymer, or a combination thereof. In some examples, the cyclosporine compound is cyclosporine A and the solvent is polyethylene glycol (15)-hydroxystearate.

Moreover, provided herein is a method for producing an aqueous cyclosporine formulation, the method comprising:

(a) placing a cyclosporine compound in a solvent at a ratio of 1:5 to 1:50 to form a first solution, wherein the solvent can be polyethylene glycol (15)-hydroxystearate, polysorbate 80, polysortabe 20, poloxamer 188, a castor oil (e.g., polyoxyethylene (35) castor oil (EL-35), and polyoxyethylene (40) castor oil (EL-40)), a hydrogenated castor oil (e.g., polyoxyethylene (35) hydrogenated castor oil (RH-35), and polyoxyethylene (40) hydrogenated castor oil (RH-40)), hydroxypropyl-β-cyclodextrin, lecithin, and a polyoxyethylene-polyoxypropylene block copolymer;

(b) mixing the first solution with water having a temperature of about 40-70° C. to producing an aqueous formulation comprising the cyclosporine compound.

In some examples, the cyclosporine compound is cyclosporine A and the solvent comprises polyethylene glycol (15)-hydroxystearate.

Further, the present disclosure features a kit for enhancing immune responses against a respiratory syncytial virus (RSV), the kit comprising: (a) a first solution comprising a respiratory syncytial virus (RSV) G protein, an immunogenic fragment thereof, or a nucleic acid encoding such; and (b) a second solution comprising one or more immune regulators dissolved in a non-ionic surfactant solvent. Suitable non-ionic surfactants include, but are not limited to, polyethylene glycol (15)-hydroxystearate, polysorbate 80, polysortabe 20, poloxamer 188, polyoxyethylene (35), a hydrogenated castor oil, hydroxypropyl-β-cyclodextrin, lecithin, a polyoxyethylene-polyoxypropylene block copolymer, or a combination thereof. In some embodiments, the RSV G protein is a modified RSV protein, for example, those disclosed herein.

In some embodiments, the first solution comprises about 10-50 μg of the RSV G protein. Alternatively or in addition, the one or more immune regulators comprise a cyclosporine compound, dexamethasone, FK506, rapamycin, or a combination thereof. In specific examples, the immune regulator is cyclosporine A, which optionally can be dissolved in polyethylene glycol (15)-hydroxystearate in some instances. In some examples, the second solution comprises about 10-50 μg of cyclosporine A dissolved in polyethylene glycol (15)-hydroxystearate.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIGS. 1A-1C include photos showing expressing of an exemplary recombinant modified RSV G protein as determined by SDS-PAGE or Western Blot. FIG. 1A: expression of the recombinant G protein in inclusion bodies in *E. coli* BL21 cells. Lane M: standard molecular weight markers. Lane 1: BL21 (pET28a-noG) without IPTG induction. Lane 2: BL21 (pET28a-noG), IPTG induction, whole cell lysis. Lane 3: BL21 (pET28a-noG), IPTG induction, cell lysis, supernatant. Lane 4: BL21 (pET28a-noG), IPTG induction, cell lysis, pellet. FIG. 1B: expression of soluble recombinant G protein in *E. coli*. Lane M: standard molecular weight markers. Lane 1: BL21 (pET28a-noG) without IPTG induction. Lane 2: BL21 (pET28a-noG), IPTG induction, whole cell lysis. Lane 3: BL21 (pET28a-noG), IPTG induction, cell lysis, supernatant. Lane 4: BL21 (pET28a-noG), IPTG induction, cell lysis, pellet. FIG. 1C: a Western Blot (WB) analysis of recombinant G protein expressed in *E. coli*. Lane 1: BL21 (pET28a-noG), IPTG induction, supernatant (soluble protein). Lane 2: BL21 (pET28a-noG), IPTG induction, cell lysis (inclusion body).

FIGS. 2A-2C are graphs showing binding of anti-RSV serum from naturally infected individuals to recombinant modified RSV G protein. FIG. 2A: anti-RSV serum from individual #2368. FIG. 2B: anti-RSV serum from individual #2666. FIG. 2C: anti-RSV serum from individual #3054.

FIGS. 3A-3B are graphs showing hemolytic effect of various RSV G-containing formulations. FIG. 3A: a picture showing appearance of red blood cell (RBC) samples incubated with the various RSV G-containing formulations as indicated. FIG. 3B: a graph showing absorbance measurements of RBC samples after incubation with the various RSV G-containing formulations as indicated.

FIG. 4 includes pictures showing local irritation after injection of immune compositions comprising RSV G protein and cyclosporine A in different solvents. Left panel: propylene as the solvent. Right panel: Kolliphor® HS 15 (polyethylene glycol (15)-hydroxystearate, a.k.a., polyethylene glycol-12-hydroxystearate) as the solvent.

FIGS. 5A-5F includes graphs showing immunoresponse induced by RSV G-protein combined with cyclosprorine A (CsA) as adjuvant. FIGS. 5A and 5B: the serum IgG titer (5A) and neutralization antibody titer (5B) of mice induced by RSV G-protein (10 µg) with different dose of CsA (0-10 µg) as an adjuvant. FIG. 5C: effects of CsA (10 µg) as adjuvant on IgG subtypes in RSV G-vaccinated mice. FIGS. 5D and 5E: effects of CsA (10 µg) as adjuvant on germinal central (GC) B cells and plasma B cells. FIG. 5F: Weight fluctuation after RSV reinfection in G+CsA-immunized group, G-immunized group and CsA-immunized group.

FIGS. 6A-6E includes graphs showing effects of recombinant G+CsA vaccination on humoral immunity, Treg cells, and Tfh cells. FIGS. 6A and 6B: amount of Treg cells (FIG. 6A) and Tfh cells (FIG. 6B) in mice treated with G+CsA vaccine, in comparison with those treated with G or CsA alone. FIG. 6C: effects of Treg cell knockout on immunization with G+CsA or G alone. FIG. 6D: effects of recombinant G protein+CsA induced Treg on humoral immunity in vivo; FIG. 6E: effects of G+CsA induced Treg on humoral immunity in vitro. FIG. 6E: identification of assistant role of G+CsA induced Treg in B cell antibody production.

FIGS. 7A-7F include graphs showing molecular mechanism of G+CsA induced Treg affecting B cell functions. FIGS. 7A and 7B; ICOS MFI in spleen Treg cells (FIG. 7A) and lymph nodes (FIG. 7B) treated by the various agents as indicated. FIGS. 7C and 7B: percentages of IL-10 (FIG. 7C) and CD40L (FIG. 7D) in Treg cells treated by the various agents as indicated. FIG. 7E: Anti-RSV antibody titer in animals treated with anti-IL10, anti-CD40L, and an isotype control antibody. FIG. 7F: IL-10 concentrations in various groups as indicated.

FIGS. 8A and 8B include graphs showing that G+CsA induced Treg cells promoted the differentiation of plasma cells and maintained a low level of B cell apoptosis.

FIGS. 9A-9F includes graphs showing protective effects of recombinant G protein plus CsA vaccination on neonate mice. FIG. 9A: weight change after RSV infection in G+CsA or G vaccinated mice. FIGS. 9B and 9C: anti-G IgG titer (FIG. 9B) and RSV neutralizing antibody titer (FIG. 9C) in G+CsA or G vaccinated mice. FIG. 9D: numbers and functions of RSV G+CsA induced Treg and GC B cell. Left upper panel indicates data from spleen at day 7; right upper panel indicates data from lymph node at day 10; left lower panel indicates data from spleen at day 7; left right panel indicates data from lymph node at day 10. FIG. 9E: CD80 (left), CD86 (middle) and MHC-II (right) expression expressed on spleen B cells in mice vaccinated with G+CsA. FIG. 9F: detection of IL-10 in mice vaccinated with recombinant G protein+CsA.

FIGS. 10A-10D include graphs showing cytokine and chemokine levels in mice vaccinated with G or G+C. 10A; lymph node levels of cytokines as indicated. 10B: tissue levels of cytokines as indicated. 10C: Lymph node levels of cytokines as indicated. 10D: tissue levels of chemokines as indicated.

FIGS. 11A-11B includes graphs showing antibody titers induced by RSV G-containing immune compositions. FIG. 11A: immunization with a recombinant modified G protein alone at different doses as indicated. FIG. 11B: immunization with the recombinant modified G protein in combination with cyclosporine A (CsA) at different doses of the G protein.

DETAILED DESCRIPTION OF THE INVENTION

Figure 1A:
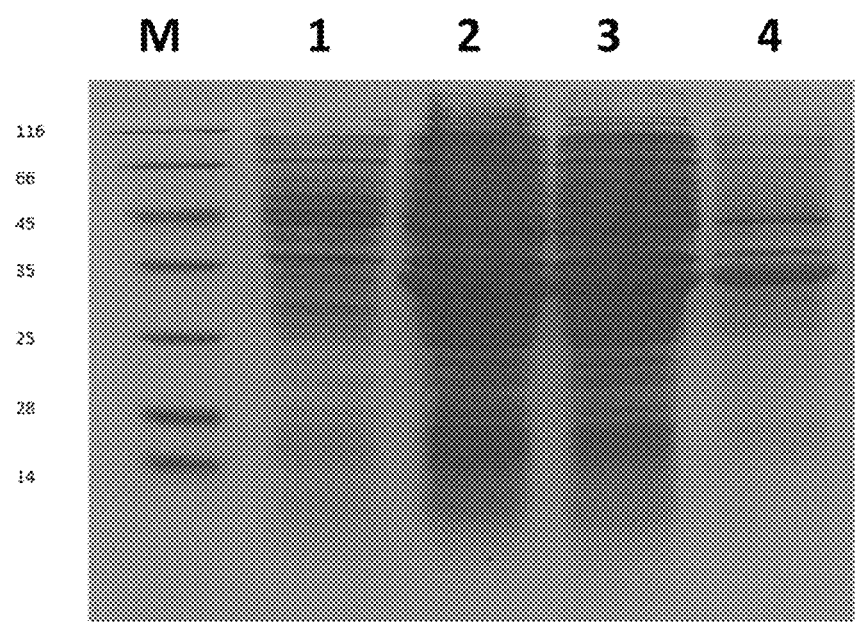
Figure 1B:
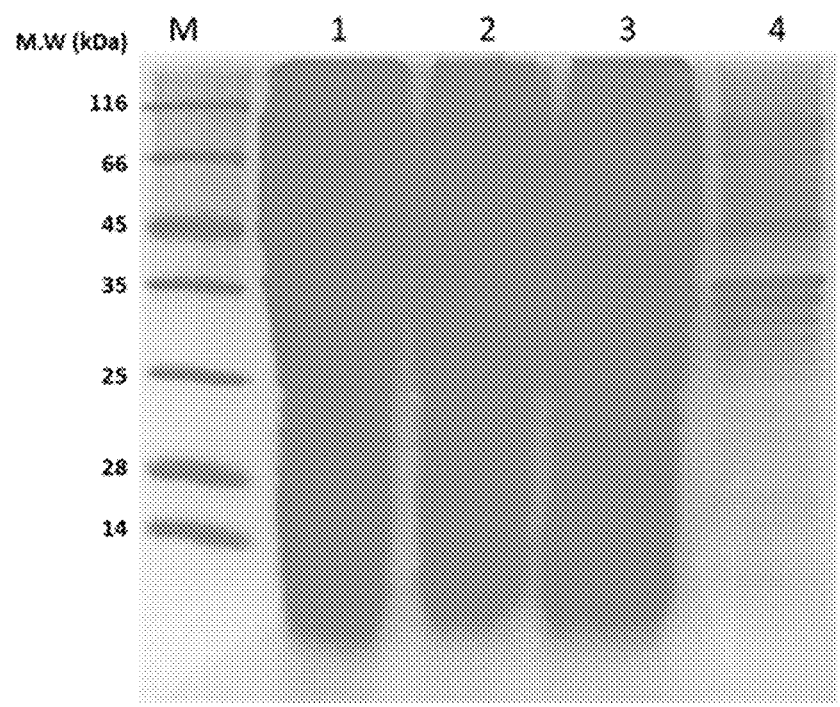
Figure 1C:
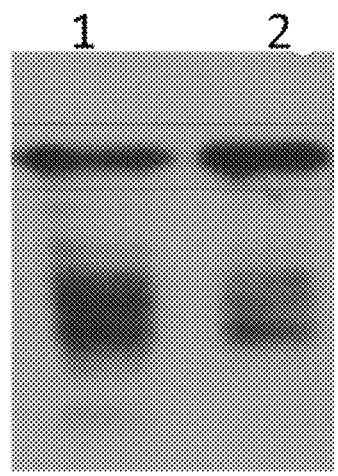
Figure 2A:
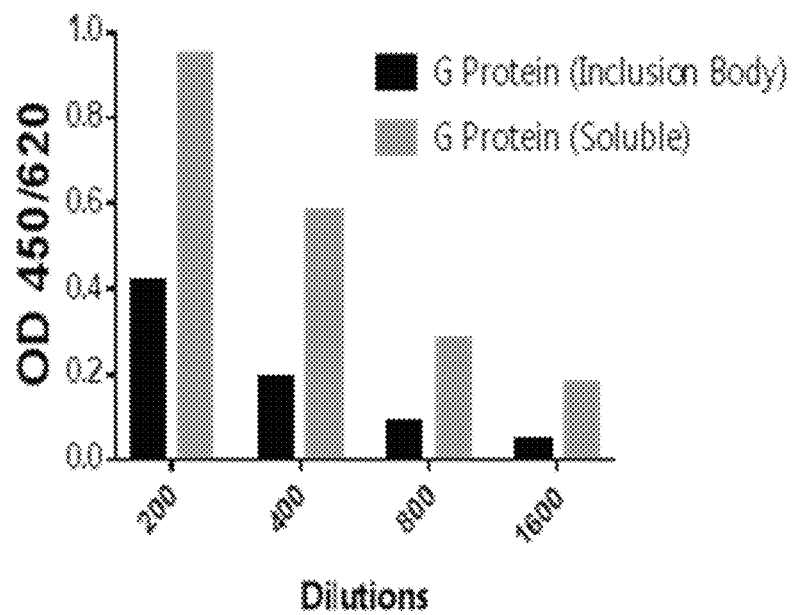
Figure 2B:
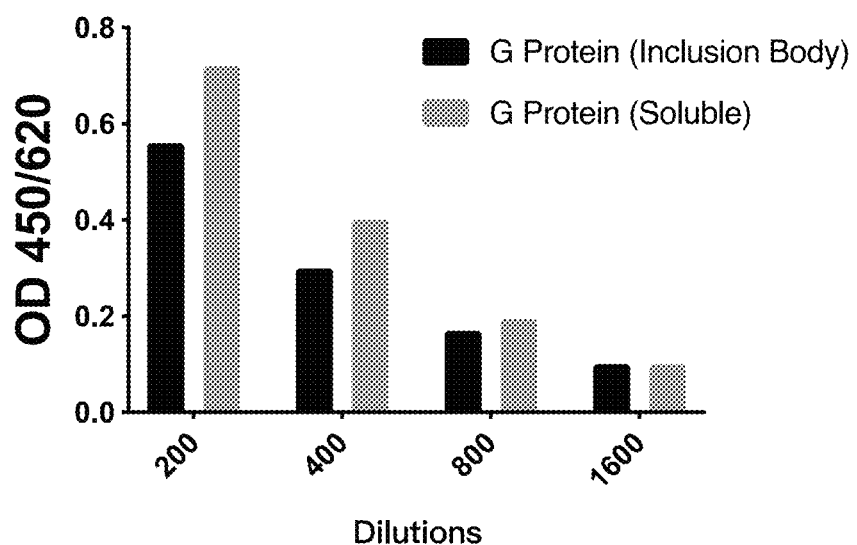
Figure 2C:
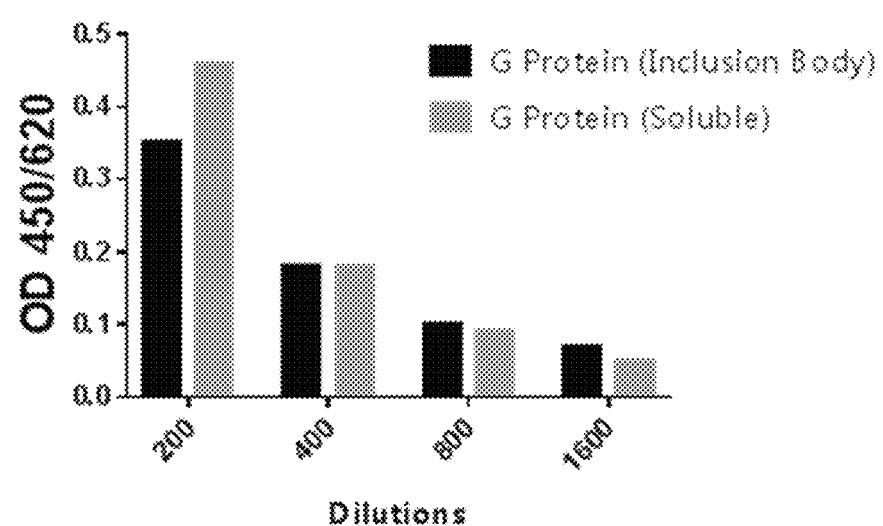

The present disclosure provides immune compositions against RSV, which possess at least two superior features: (i) elicit higher levels of neutralizing antibodies against RSV; and (ii) reduce inflammatory response in lung caused by T cells via, e.g., induction of regulatory T cells ($T_{reg}$ cells). As shown in the Examples below, exemplary immune compositions disclosed herein showed high activity in inducing neutralization antibodies specific to RSV, inducing RSV-specific regulatory T (Treg) cells, enhancing levels of IL-10 and/or CD40L in RSV-specific Treg cells, and/or reducing pathologic T cell responses associated with RSV infection.

I. Immune Compositions Comprising RSV G Proteins

The anti-RSV immune compositions described herein comprise one or more RSV G polypepitdes, one or more immune regulator(s), and optionally a suitable solvent that can form an aqueous solution with the immune regulator(s) to dissolve the RSV G polypeptide.

(A) RSV G Polypeptide

RSV G protein, also known as the attachment glycoprotein, is a major surface glycoprotein of RSV and binds to CX3CR1 on human airway epithelial cells to mediate viral attachment and subsequent infection.

In some embodiments, a wild-type RSV G protein or an antigenic fragment thereof can be used for making the immune compositions disclosed herein. Wild-type RSV G proteins are well known in the art. For example, an exemplary amino acid sequence of a wild-type RSV G protein can be found under GenBank accession no. CAA34937 (provided below as SEQ ID NO:9 with the N-terminal transmembrane domain in boldface).

```
  1   msknkdqrta ktlektwdtl nyllfissgl yklnlksiaq itlsilamii stsliitaii 61   fiasanhkvt lttaiiqdat sqiknttpty ltqdpqlgis fsnlseitsq tttilasttp 121   gvksnlqptt vktkntttq tqpskpttkq rqnkppnkpn ndfhfevfnf vpcsicsnnp 181   tcwaickrip nkkpgkkttt kptkkptfkt tkkdlkpqtt kpkevpttkp teeptinttk 241   tnitttlltn nttgnpklts qmetfhstss egnlspsqvs ttsehpsqps sppnttrq
```

Other naturally-occurring RSV G proteins are known to those skilled in the art and can be identified in publically available databases, for example, GenBank, using SEQ ID NO:9 as a query.

In some embodiments, the RSV G polypeptide used in the immune compositions disclosed herein may be a modified form of a wild-type counterpart. For example, the modified RSV G polypeptide may be a truncated form of a wild-type RSV G protein lacking the N-terminal transmembrane domain or a portion thereof. In one example, the truncated form may lack the N-terminal 1-66 amino acid residues of SEQ ID NO:9. Such a truncated form may contain the amino acid sequence of SEQ ID NO:1 (corresponding to residues 67-298 of SEQ ID NO:9).

```
                                                    (SEQ ID NO: 1)
hkvt lttaiiqdat sqiknttpty ltqdpqlgis fsnlseitsq tttilasttp gvksnlqptt vktkntttq tqpskpttkq rqnkppnkpn ndfhfevfnf vpcsicsnnp tcwaickrip nkkpgkkttt kptkkptfkt tkkdlkpqtt kpkevpttkp teeptinttk tnitttlltn nttgnpklts qmetfhstss egnlspsqvs ttsehpsqps sppnttrq
```

Alternatively or in addition, the modified RSV G protein may contain one or more mutations at one or more positions of a naturally-occurring RSV G protein, for example, in SEQ ID NO:1. A number of exemplary modified RSV G polypeptides are provided below:

```
Modified RSV G protein 1(2)-SEQ ID NO: 2 (encoded
by the nucleotide sequences of SEQ ID NOs: 5 and
6 provided below)
HKVTLTTAIIQDATSQIKNTTPTYLTQDPQLGISFSNLSEITSQTTTI

LASTTPGVKSNLQPTTVKTKNTTTTQTQPSKPTTKQRQNKPPNKPNND

SHSEVSNSVPSSICSNNPTCWAISKRIPNKKPGKKTTTKPTKKPTFKT

TKKDLKPQTTKPKEVPTTKPTEEPTINTTKTNITTTLLTNNTTGNPKL

TSQMETFHSTSSEGNLSPSQVSTTSEHPSQPSSPPNTTRQ

Modified RSV G protein 3-SEQ ID NO: 3 (encoded by
the nucleotide sequences of SEQ ID NO: 7
provided below)
HKVTLTTAIIQDATSQIKNTTPTYLTQDPQLGISFSNLSEITSQTTTI

LASTTPGVKSNLQPTTVKTKNTTTTQTQPSKPTTKQRQNKPPKKPKDD

YHFEVFNFVPCSICGNNQLCKSICKTIPSNKPKKKTTTKPTKKPTFKT

TKKDLKPQTTKPKEVPTTKPTEEPTINTTKTNITTTLLTNNTTGNPKL

TSQMETFHSTSSEGNLSPSQVSTTSEHPSQPSSPPNTTRQ

Modified RSV G protein 4-SEQ ID NO: 4 (encoded
by the nucleotide sequences of SEQ ID NO: 8
provided below)
HKVTPTTAIIQDATSQIKNTTPTYLTQNPQLGISPSNPSEITSQITTI

LASTTPGVKSTLQSTTVKTKNTTTTQTQPSKPTTKQRQNKPPSKPNND

FHFEVFNFVPCSICSNNPTCWAICKRIPNKKPGKKTTTKPTKKPTLKT

TKKDPKPQTTKSKEVPTTKPTEEPTINTTKTNIITTLLTSNTTGNPEL

TSQMETFHSTSSEGNPSPSQVSTTSEYPSQPSSPPNTPRQ
```

Provided below is a sequence alignment of the exemplary modified RSV G proteins described above relative to SEQ ID NO:1 (WT) (SEQ ID NOs: 1-4, from top to bottom). Mutated positions are identified in boldface.

```
WT    HKVTLTTAII QDATSQIKNT TPTYLTQDPQ LGISFSNLSE ITSQTTTILA STTPGVKSNL   60
1(2)  HKVTLTTAII QDATSQIKNT TPTYLTQDPQ LGISFSNLSE ITSQTTTILA STTPGVKSNL   60
3     HKVTLTTAII QDATSQIKNT TPTYLTQDPQ LGISFSNLSE ITSQTTTILA STTPGVKSNL   60
4     HKVTPTTAII QDATSQIKNT TPTYLTQNPQ LGISPSNPSE ITSQITTILA STTPGVKSTL   60

WT    QPTTVKTKNT TTTQTQPSKP TTKQRQNKPP NKPNNDFHFE VFNFVPCSIC SNNPTCWAIC  120
1(2)  QPTTVKTKNT TTTQTQPSKP TTKQRQNKPP NKPNNDSHSE VSNSVPSSIC SNNPTCWAIS  120
3     QPTTVKTKNT TTTQTQPSKP TTKQRQNKPP KKPKDDYHFE VFNFVPCSIC GNNQLCKSIC  120
4     QSTTVKTKNT TTTQTQPSKP TTKQRQNKPP SKPNNDFHFE VFNFVPCSIC SNNPTCWAIC  120

WT    KRIPNKKPGK KTTTKPTKKP TFKTTKKDLK PQTTKPKEVP TTKPTEEPTI NTTKTNITTT  180
1(2)  KRIPNKKPGK KTTTKPTKKP TFKTTKKDLK PQTTKPKEVP TTKPTEEPTI NTTKTNITTT  180
3     KTIPSNKPKK KTTTKPTKKP TFKTTKKDLK PQTTKPKEVP TTKPTEEPTI NTTKTNITTT  180
4     KRIPNKKPGK KTTTKPTKKP TLKTTKKDPK PQTTKSKEVP TTKPTEEPTI NTTKTNIITT  180
```

```
WT      LLTNNTTGNP  KLTSQMETFH  STSSEGNLSP  SQVSTTSEHP  SQPSSPPNTT  RQ      232
1(2)    LLTNNTTGNP  KLTSQMETFH  STSSEGNLSP  SQVSTTSEHP  SQPSSPPNTT  RQ      232
3       LLTNNTTGNP  KLTSQMETFH  STSSEGNLSP  SQVSTTSEHP  SQPSSPPNTT  RQ      232
4       LLTSNTTGNP  ELTSQMETFH  STSSEGNPSP  SQVSTTSEYP  SQPSSPPNTP  RQ      232
```

The modified RSV G proteins may contain one or more positions as identified above, for example, L5, D28, F35, L38, T45, N59, P62, N91, N94, N95, F97, F99, F102, F104, C107, S111, P114, T115, W117, A118, C120, R122, N125, G129, F142, L149, P156, T178, N184, K191, L208, H219, and/or T230 in SEQ ID NO:1. In some instances, the modified RSV G proteins may contain one or more amino acid substitutions as identified above, for example, L5P, D28N, F35P, L38P, T45I, N59T, P62S, N91K, N91S, N94K, N95D, F97S, F97Y, F99S, F102S, F104S, C107S, S111G, P114Q, T115L, W117K, A118S, C120S, R122T, N125S, G129K, F142L, L149P, P156S, T178I, N184S, K191E, L208P, H219Y, and/or T230P.

In some examples, the modified RSV G protein may comprise one or more mutations of: (a) C97S, F99S, F102S, F104S, C107S, and/or C120S; (b) N91K, N94K, N95D, F97Y, S111G, P114Q, T115L, W117K, A118S,R122T, N125S, and/or G129K; or (c) L5P, D28N, F35P, L38P, T45I, N59T, P62S, N91S, F142L, L149P, P156S, T178I, N184S, K191E, L208P, H219Y, and/or T230P.

Any of the RSV G polypeptides disclosed herein, naturally occurring or modified, may share a sequence identity at least 85% to SEQ ID NO:1 (e.g., at least 90%, at least 95%, at least 97%, or above). The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some instances, the modified RSV G polypeptide disclosed herein may comprise one or more conservative amino acid residue substitutions relative to its wild-type counterpart. In some examples, the conservative amino acid residue substitutions may occur outside the mutation positions disclosed above. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Any of the RSV G polypeptides described herein can be prepared by the conventional recombinant technology. See, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Briefly, a nucleic acid comprising a coding sequence of the RSV G polypeptide disclosed herein may be cloned into a suitable expression vector, which can be transfected into a suitable host cell for expression of the recombinant RSV G polypeptide. In some instances, the nucleic acid encoding the RSV G polypeptide, which may be in operable linkage to a suitable promoter for driving the expression of the RSV G protein, may be used in the immune compositions disclosed herein. Once delivered to a subject, the nucleic acid can express the RSV G polypeptide, which can elicit immune responses. See also description below. Any of the modified RSV G polypeptide disclosed herein, nucleic acids (e.g., expression vectors) encoding such, and host cells comprising such nucleic acids are also within the scope of the present disclosure.

(B) Immune Compositions

The immune compositions described herein may comprise one or more RSV G polypeptides as disclosed herein, an immunogenic fragment thereof, or one or more nucleic acids encoding the RSV G polypeptides. Such nucleic acids are also within the scope of the present disclosure.

In some embodiments, the RSV G polypeptide is a modified version relative to the wild-type polypeptide counterpart, such as those disclosed herein. In some examples, the RSV G polypeptide for use in making the immune compositions provided herein comprises (e.g., consists of) SEQ ID NO:1. In some embodiments, the RSV G polypeptide is a modified version relative to the wild-type polypeptide counterpart, such as those disclosed herein. In some examples, the RSV G polypeptide for use in making the immune compositions provided herein comprises (e.g., consists of) SEQ ID NO:2 (encoded by the nucleotide sequences of SEQ ID NO:5 or 6). In some embodiments, the RSV G polypeptide is a modified version relative to the wild-type polypeptide counterpart, such as those disclosed herein. In some examples, the RSV G polypeptide for use in making the immune compositions provided herein comprises (e.g., consists of) SEQ ID NO:3 (encoded by the nucleotide sequence of SEQ ID NO:7). In some embodiments, the RSV G polypeptide is a modified version relative to the wild-type polypeptide counterpart, such as those disclosed herein. In some examples, the RSV G polypeptide for use in making the immune compositions provided herein comprises (e.g., consists of) SEQ ID NO:4 (encoded by the nucleotide sequence of SEQ ID NO:8).

In addition, the immune compositions may further comprise one or more immune regulators, which are agents capable of modulating immune responses. In some embodiments, the one or more immune regulator(s) may be an immune suppressant, for example, a cyclosporine compound, dexamethasone, FK506, rapamycin, or a combination thereof.

In one example, the immune compositions disclosed herein comprises a cyclosporine compound, such as cyclosporine A (CsA). A cyclosporine compound is a lipophilic cyclic polypeptide of about 11 amino acid residues. Cyclosporine compounds typically possess immunosuppressant activity. Cyclosporin A is a cyclic nonribosomal peptide of eleven amino acids, which is an immunosuppressant drug widely used in post-allogeneic organ transplant to reduce the activity of the patient's immune system.

In some embodiments, the immune composition disclosed herein may comprise a cyclosporine compound such as CsA and a modified RSV G polypeptide as also disclosed herein (e.g., the modified RSV G polypeptide of SEQ ID NO:1, 2, 3, or 4) at a ratio of 10:1 to 1:10 (e.g., 10:1 to 5:1, 10:1 to 2:1, 1:1 to 1:10, 1:1 to 1:5, or 2:1 to 1:2) by weight in the immune composition. In some examples, the weight ratio of CsA to the modified RSV G polypeptide is 2:1. In some examples, the weight ratio of CsA to the modified RSV G polypeptide is 1:1. In some examples, the weight ratio of CsA to the modified RSV G polypeptide is 1:2.

The immune compositions disclosed herein may further comprise a suitable solvent, which may be able to dissolve a poorly soluble cyclosporine compound. Suitable solvent includes a non-ionic surfactant, such as a cyclodextrin (e.g., hydroxypropyl-β-cyclodextrin), a lecithin, a polyethylene glycol, or a combination thereof. In some embodiments, the solvent comprises a non-ionic surfactant. In some examples, the non-ionic surfactant is polyethylene glycol (15)-hydroxystearate (a.k.a., macrogol 15 hydroxystearate, tradename Kolliphor® HS 15). Other exemplary non-ionic surfactants include, but are not limited to, polysorbate 80 (Tween® 80), polysorbate 20 (Tween® 20), a polyoxyethylene-polyoxypropylene block copolymer (e.g., poloxamer 188 or Pluronic® F68), a castor oil (e.g., polyoxyethylene (35) castor oil (EL-35), and polyoxyethylene (40) castor oil (EL-40)), a hydrogenated castor oil (e.g., polyoxyethylene (35) hydrogenated castor oil (RH-35), polyoxyethylene (40) hydrogenated castor oil (RH-40)), or a combination thereof.

Further, the immune compositions as disclosed herein may comprise one or more adjuvant. An adjuvant refers to a substance that is co-used with an antigen to help stimulate and enhance the immune responses elicited by the antigen. Examples include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol.

Methods for preparing immune compositions are generally well known in the art, as exemplified by U.S. Pat. Nos. 4,601,903; 4,599,231; 4,599,230; and 4,596,792. Immune compositions may be prepared as injectables, as liquid solutions, or emulsions. The RSV G polypeptide as disclosed herein and one or more immune regulators, which may be dissolved in a suitable solvent as also described herein, may be mixed with physiologically acceptable and compatible excipients. The excipient must be "acceptable" in the sense that it is compatible with the active ingredient of the composition, and preferably, capable of stabilizing the active ingredient and not deleterious to the subject to be treated. The excipient is selected on the basis of the mode and route of administration, and standard pharmaceutical practice. Suitable pharmaceutical excipient and diluents, as well as pharmaceutical necessities for their use, are described in Remington's Pharmaceutical Sciences. Excipients may include, water, saline, dextrose, glycerol, ethanol, a suitable solvent for dissolving the immune regulators (e.g., CsA) such as those disclosed herein, and combinations thereof. The immune composition may further contain minor amounts of auxiliary substances such as wetting or emulsifying agents, pH buffering agents, or adjuvants to enhance the effectiveness of the vaccines. Methods of achieving adjuvant effect for the immune compositions include use of agents, such as aluminum hydroxide or phosphate (alum), commonly used as 0.05 to 0.1 percent solutions in phosphate buffered saline.

When CsA is used as the immune regulator in the immune composition disclosed herein, the following method may be used for preparation to address the poor water solubility issue of CsA, to better dissolve the RSV G polypeptide, or both. See also Example 1 below. Briefly, CsA may be dissolved in a suitable solvent (e.g., Kolliphor® HS 15) at a suitable CsA:solvent weight ratio, for example, 1:5 to 1:50 (e.g., 1:5-1:20, 1:10-1:40, or 1:20-1:50) to form a solution. Water or an aqueous solution can then be mixed with the CsA/solvent (e.g., Kolliphor® HS 15) solution to form an aqueous solution. The resultant solution can be used to dissolve RSV G polypeptides (e.g., lyophilized). Methods of making aqueous solutions of CsA and the resultant aqueous solutions are also within the scope of the present disclosure.

Any of the immune compositions may be in the form of solutions, suspensions, tablets, pills, capsules, sustained release formulations or powders and contain 10-95% of the RSV G polypeptides as disclosed herein. In some embodiments, the immune composition can be a dosage form (unit doses), which refers to the physical form of a dose of an active agent (e.g., the RSV G polypeptide) used as a drug or medication intended for administration or consumption. Common dosage forms include, but are not limited to, pill, tablet, capsule, drink, syrup, aerosol, inhaler, liquid injection, pure powder, or solid crystal. In some examples, the dosage form of the immune composition may comprise a RSV G polypeptide (e.g., a modified version such as one of SEQ ID NOs:1-4) and CsA at a weight ratio of 2:1 to 1:2 (e.g., 1:1). Polyethylene glycol (15)-hydroxystearate (Kolliphor® HS 15) may be used as the non-ionic surfactant in such an immune composition. In some examples, the dosage form may comprise about 10-50 μg (e.g., about 10-20 μg, about 20-30 μg, about 30-40 μg, or about 40-50 μg) the RSV G polypeptide and about 10-50 μg (e.g., about 10-20 μg, about 20-30 μg, about 30-40 μg, or about 40-50 μg) CsA. In specific examples, the dosage form may comprise about 10 μg RSV G polypeptide and about 10 μg CsA. In other examples, the dosage form may comprise about 50 μg RSV G polypeptide and about 50 μg CsA.

II. Therapeutic Applications

Any of the immune compositions may be used for eliciting immune responses against RSV, including treatment usages and prophylactic uses. To practice the methods described herein, an effective amount of the immune composition as disclosed herein can be administered to a subject in need of the treatment via a suitable route. For example, the immune composition may be administered parenterally, by injection subcutaneously, or intramuscularly. Alternatively, other modes of administration including suppositories and oral formulations may be desirable.

"An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The immune compositions are administered in effective amounts. An "effective amount" may refer to the amount of the RSV G protein in the composition that alone, or together with further doses, produces the desired response, e.g., increases an immune response to RSV. Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The immune composition can be administered in a manner compatible with the dosage formulation, and in an amount that is therapeutically effective, protective, and immunogenic. Particularly, the amount of the RSV G polypeptide in the composition must be sufficient for inducing a high titer of neutralizing antibodies and optionally reducing T cell responses. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

In some examples, about 0.1 µg to about 500 µg (e.g., about 1 µg to about 300 µg or about 10 µg to about 100 µg) of the RSV G polypeptide (e.g., a modified version such as one of SEQ ID NOs:1-4) may be given to a subject to elicit immune responses against RSV. The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

For the purpose of the present disclosure, the appropriate dosage of any of the immune compositions as described herein will depend on the specific RSV G polypeptide and/or the immune regulator employed, the type and severity of the disease/disorder, whether the immune composition is administered for preventive or therapeutic purposes, previous therapy, the patient's clinical history and response to the agonist, and the discretion of the attending physician. Typically the clinician will administer an antibody, until a dosage is reached that achieves the desired result. In some embodiments, the desired result is an increase in anti-RSV immune response (preferably systemic). Methods of determining whether a dosage resulted in the desired result would be evident to one of skill in the art. Administration of immune compositions may be repeated for multiple times (e.g., 2 times or 3 times), depending, for example, upon the recipient's physiological condition, whether the purpose of the administration is therapeutic or prophylactic, and other factors known to skilled practitioners. The administration of the immune composition may be essentially continuous over a preselected period of time or may be in a series of spaced dose, e.g., either before, during, or after developing a target disease or disorder.

The subject to be treated by the methods disclosed herein may be a human subject. Such a human subject may be an infant, a young child (e.g., <5 years old), an adult, or an elderly (>65 years). In some instances, the human subject may have been infected with RSV. In other instances, the human subject may be suspected of having RSV infection, for example, showing one or more symptoms associated with RSV infection. Alternatively, the human subject may be a healthy subject but may be at risk for RSV infection. The immune compositions disclosed herein may be used for prophylactic purposes.

A subject having RSV infection can be identified by routine medical examination, e.g., laboratory tests, organ functional tests, and/or other medical examinations known to medical practitioners. In some embodiments, the subject to be treated by the method described herein may be a human patient who has undergone or is subjecting to an anti-infection therapy, for example, involving one or more antibiotics.

A subject suspected of having any of such target disease/disorder might show one or more symptoms of the disease/disorder. A subject at risk for the disease/disorder can be a subject having one or more of the risk factors for that disease/disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

Conventional methods, known to those of ordinary skill in the art of medicine, can be used to administer the pharmaceutical composition to the subject, depending upon the type of disease to be treated or the site of the disease. This immune composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

In some embodiments, the immune composition disclosed herein may be prepared at a point-of-care (where the immune composition is given to a subject) by mixing a first solution comprising the RSV G polypeptide (e.g., a modified version such as one of SEQ ID NOs:1-4) and a second solution comprising the one or more immune regulator (e.g., CsA) dissolved in the suitable solvent (e.g., a non-ionic surfactant such as polyethylene glycol (15)-hydroxystearate).

Treatment efficacy for the target disease/disorder as disclosed herein can be assessed by methods well-known in the art.

III. Kits for Use in Enhancing Immune Responses Against RSV Infection

The present disclosure also provides kits for use in enhancing immune responses against RSV. Such kits can include one or more containers comprising any of the immune compositions disclosed herein, or components thereof for producing the immune composition. In some embodiments, the kit comprises at least two containers. A first container comprises a solution comprising a RSV G polypeptide, e.g., any of those described herein (e.g., a modified RSV G polypeptide such as one of SEQ ID NOs: 1-4). A second container comprises a solution comprising one or more immune regulators (for example, CsA), which is dissolved in a suitable solvent, for example, one of the non-ionic surfactants disclosed herein. When CsA is used, the solvent can be polyethylene glycol (15)-hydroxystearate.

In some embodiments, the kit can comprise instructions for use in accordance with any of the methods described herein. The included instructions can comprise a description of administration of the immune composition to treat, delay the onset, or alleviate a target disease as those described herein (e.g., RSV infection). The kit may further comprise instructions for producing the immune composition before the administration. Alternatively or in addition, the kit may further comprise a description of selecting an individual suitable for treatment based on identifying whether that individual has, suspected of having, or is at risk for RSV infection.

The instructions relating to the use of an immune composition as disclosed herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease. Instructions may be provided for practicing any of the methods described herein.

The kits of the present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an RSV G polypeptide as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; Oligonucleotide Synthesis (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobi-* lized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Preparation of Respiratory Syncytial Virus (RSV) Vaccine

Materials and Methods

The experimental methods used in the following examples are conventional methods unless noted otherwise. The materials, reagents used in the following examples are commercially available unless noted otherwise. Electro-chemiluminescence (ECL) reagent is a product of GE Healthcare Europe, Sweden.

Method for preparation of inactive vaccine (FI-RSV): $10^7$ $TCID_{50}$ of RSV virus (ATCC, catalog no. VR-26TM) was incubated with formaldehyde for 72 hours at 37° C. and then centrifuged at 50,000 g for 1 hour at 2-8° C.

Cyclosporine A (CsA) is the product of Taishan Chemical Pharmaceutical Co. Inc or Fujian Kerui Pharmaceutical Co. Inc.

The vector of pET28a (+) is a product of Novagen, and the catalog number is 69864-3.

Escherichia coli of BL21 (DE3) is a product of Tiangen Biochemical Technology (Beijing) Co. Inc, and the catalog number is CB105-02.

RPMI1640 medium is the product of Maichen Technology Co. Inc, and the catalog number is CM10040.

Goat anti-RSV polyclonal antibody is a product of Meridian, USA, and the catalog number is B656860G.

A. Production of Recombinant G Protein

1) Optimization of Artificial Nucleotide Sequences Encoding Modified RSV G Proteins The following four nucleotide sequences were designed for expressing the encoded modified RSV G proteins. SEQ ID NO:5 and SEQ ID NO:6 encode the same RSV G protein (having the amino acid sequence of SEQ ID NO:2 provided above). SEQ ID NOs:7 and 8 encode the modified RSV G proteins of SEQ ID NO:3 and SEQ ID NO:4 respectively. Some of these coding sequences have been codon optimized for expression in E. coli cells,

```
                                          SEQ ID NO: 5
CATAAGGTGACCCTGACTACTGCTATCATCCAGGACGCAACTAGCCAAA

TCAAAAACACCACGCCGACCTACCTGACTCAGGATCCTCAGCTGGGTAT

CAGCTTCAGCAACCTGTCTGAGATCACTTCTCAGACTACGACGATCCTG

GCCTCTACCACTCCAGGTGTAAAATCCAACCTGCAGCCAACCACCGTGA

AAACCAAAAATACCACTACCACCCAGACCCAGCCGTCTAAACCAACTAC

GAAACAGCGTCAGAACAAACCGCCTAACAAACCAAACAACGACTCCCAC

TCCGAGGTCTCTAACTCCGTTCCGTCCTCTATCTGTTCTAACAACCCGA

CTTGCTGGGCGATTTCTAAACGCATTCCGAACAAGAAACCTGGTAAAAA
```

```
                                          -continued
GACCACCACGAAACCGACGAAAAAGCCGACCTTCAAAACCACCAAGAAA

GATCTGAAACCGCAGACCACTAAACCGAAAGAAGTTCCGACGACCAAAC

CGACCGAAGAACCGACCATTAATACCACCAAAACCAACATTACCACCAC

TCTGCTGACGAACAACACCACTGGCAACCCGAAACTGACCTCCCAGATG

GAAACCTTTCACAGCACCTCCAGCGAAGGCAATCTGTCCCCGTCCCAGG

TTAGCACCACTAGCGAACACCCGAGCCAACCGTCTTCTCCGCCGAACAC

TACTCGTCAA

SEQ ID NO: 6
CACAAAGTCACACTAACAACTGCAATCATACAAGATGCAACAAGCCAGA

TCAAGAACACAACCCCAACATACCTCACTCAGGATCCTCAGCTTGGAAT

CAGCTTCTCCAATCTGTCTGAAATTACATCACAAACCACCACCATACTA

GCTTCAACAACACCAGGAGTCAAGTCAAACCTGCAACCCACAACAGTCA

AGACTAAAAACACAACAACAACCCAAACACAACCCAGCAAGCCCACTAC

AAAACAACGCCAAAACAAACCACCAAACAAACCCAATAATGATAGTCAC

AGTGAAGTGAGTAACAGTGTACCCAGTAGCATATGCAGCAACAATCCAA

CCTGCTGGGCTATCAGTAAAAGAATACCAAACAAAAAACCAGGAAAGAA

AACCACCACCAAGCCTACAAAAAAACCAACCTTCAAGACAACCAAAAAA

GATCTCAAACCTCAAACCACTAAACCAAAGGAAGTACCCACCACCAAGC

CCACAGAAGAGCCAACCATCAACACCACCAAAACAAACATCACAACTAC

ACTGCTCACCAACAACACCACAGGAAATCCAAAACTCACAAGTCAAATG

GAAACCTTCCACTCAACCTCCTCCGAAGGCAATCTAAGCCCTTCTCAAG

TCTCCACAACATCCGAGCACCCATCACAACCCTCATCTCCACCCAACAC

AACACGCCAGTAG

SEQ ID NO: 7
CACAAAGTCACACTAACAACTGCAATCATACAAGATGCAACAAGCCAGA

TCAAGAACACAACCCCAACATACCTCACTCAGGATCCTCAGCTTGGAAT

CAGCTTCTCCAATCTGTCTGAAATTACATCACAAACCACCACCATACTA

GCTTCAACAACACCAGGAGTCAAGTCAAACCTGCAACCCACAACAGTCA

AGACTAAAAACACAACAACAACCCAAACACAACCCAGCAAGCCCACTAC

AAAACAACGCCAAAACAAACCACCAAACAAACCCAATAATGATTTTCAC

TTCGAAGTGTTTAACTTTGTACCCTGCAGCATATGCAGCAACAATCCAA

CCTGCTGGGCTATCTGCAAAAGAATACCAAACAAAAAACCAGGAAAGAA

AACCACCACCAAGCCTACAAAAAAACCAACCTTCAAGACAACCAAAAAA

GATCTCAAACCTCAAACCACTAAACCAAAGGAAGTACCCACCACCAAGC

CCACAGAAGAGCCAACCATCAACACCACCAAAACAAACATCACAACTAC

ACTGCTCACCAACAACACCACAGGAAATCCAAAACTCACAAGTCAAATG

GAAACCTTCCACTCAACCTCCTCCGAAGGCAATCTAAGCCCTTCTCAAG

TCTCCACAACATCCGAGCACCCATCACAACCCTCATCTCCACCCAACAC

AACACGCCAGTAG

SEQ ID NO: 8
CATAAAGTAACCCCGACCACCGCTATCATCCAGGACGCTACCAGCCAGA

TCAAAAACACTACGCCTACCTATCTGACTCAGAACCCGCAACTGGGCAT
```

-continued

```
CTCCCCGTCCAATCCGTCTGAAATTACCTCCCAGATCACTACCATCCTG

GCATCCACTACTCCGGGTGTGAAATCTACCCTGCAGTCCACTACCGTAA

AAACGAAAAACACCACCACTACCCAGACTCAGCCTTCCAAACCTACTAC

GAAACAGCGTCAGAACAAACCGCCGAGCAAACCGAACAACGACTTCCAC

TTTGAAGTTTTCAACTTCGTCCCATGCAGCATTTGTAGCAACAATCCGA

CCTGCTGGGCAATTTGCAAACGCATCCCAAACAAAAAGCCGGGCAAAAA

GACGACCACTAAACCAACCAAGAAACCTACCCTGAAAACTACCAAAAAA

GACCCGAAACCGCAGACCACCAAATCTAAAGAAGTTCCGACGACCAAAC

CGACCGAGGAACCGACGATCAACACCACGAAAACGAACATCATCACCAC

CCTGCTGACCTCTAACACTACCGGTAATCCGGAGCTGACTAGCCAGATG

GAAACCTTTCACAGCACTTCTTCTGAAGGTAACCCATCTCCGAGCCAGG

TGTCCACCACTTCTGAATACCCGAGCCAACCGTCCTCCCCGCCTAATAC

GCCGCGTCAA
```

2) Construction of Expression Vector pET28a-noG

SEQ ID NO:8 (encoding SEQ ID NO:4) was used as an exemplary RSV G protein-encoding gene for expression the RSV G protein in *E. coli*. This sequence was designed by codon optimizing a consensus RSV G-coding sequence from a group of RSV genotype A1 viral sequences for *E. coli* expression. Nucleic acids having the sequence of SEQ ID NO:8 was synthesized chemically and subcloned into *E. coli* vector pET28a (+) at the restriction sites of Nco I and Xho I. After digestion and ligation, the recombinant construct was acquired and named as the pET28a-noG. "noG" represents tag-free G protein.

3) Generating Recombinant Bacteria Cells Carrying pET28a-noG

The pET28a-noG plasmid was then transformed into *E. coli* BL21 (DE3) via conventional methods. The resultant recombinant bacterium strain was named BL21 (DE3)/pET28a-noG. BL21 (DE3) transformed with pET28a (+) empty vector was used as a control (BL21 (DE3)/pET-28a (+)).

4) Expression of Recombinant RSV G Protein in Inclusion Bodies

The expression of recombinant G protein was induced by adding of different concentrations of Isopropyl β-D-Thiogalactoside (IPTG) during the bacteria culture. The steps were listed as follows: a single colony of BL21(DE3)/pET28a-noG was picked up and inoculated into LB medium at 37° C. The medium was cultured to logarithmic growth phase ($OD_{600nm}$=0.5), and IPTG was added at a final concentration of 0.5 mmol/L, 1 mmol/L, 2 mmol/L, 3 mmol/L, or 5 mmol/L, respectively, and induced at 37° C. for 1-4 hours respectively. After the induction, the bacteria were collected, washed with PBS, sonicated and centrifuged at 10,000 rpm. The supernatant and the resuspended pellet (inclusion body) were detected by SDS-PAGE to verify protein expression. The results are shown in FIG. 1A.

These results demonstrate that *E. coli* BL21 (DE3) transformed with the recombinant plasmid pET28a-noG effectively expressed RSV recombinant G protein (about 35 kDa) under the conditions of 37° C., 0.5 mM IPTG for 4 hours.

5) Expression of Soluble Recombinant RSV G Protein

The expression of RSV recombinant G protein was induced by Isopropyl β-D-Thiogalactoside (IPTG). The steps were as follows: a single colony of BL21(DE3)/pET28a-noG was picked, inoculated into LB medium, and cultured at 37° C. In the logarithmic growth phase ($OD_{600nm}$=0.5), IPTG was added at a final concentration of 0.5 mmol/L, and induced at 30° C. for 1-4 hours.

After the IPTG induction, bacteria were collected and sonicated before being subjected into a centrifugation at 12,000 rpm for 10 min. The supernatant and the resuspended pellet were separately detected by SDS-PAGE to verify protein expression. The results are showed in the FIG. 1B. The *E. coli* BL21 (DE3) transformed with the recombinant plasmid pET28a-G expressed soluble RSV recombinant G protein (about 35 kDa) under the condition of 30° C., 0.5 mM IPTG for 4 hours.

B. Antigenicity Analysis of Recombinant RSV G Protein

The recombinant RSV G protein (SEQ ID NO:4) obtained following the above descriptions was separated on a 12% SDS-PAGE gel, and then was transferred to the PVDF membrane using a Bio-Rad transmembrane system. The membrane was immersed in PBST supplemented with 5% skim milk powder and blocked at 37° C. for 2 hours. After being washed with PBST for three times, the membrane was transferred into the solution of goat anti-RSV polyclonal antiserum (Meridian, USA) in PBST supplemented with 5% skim milk powder with 2,000 times dilution. Then the membrane was incubated for 1 hour and washed 3 times with PBST. The membrane was immersed in solution of HRP bovine anti-goat IgG in PBST supplemented with 5% skim milk powder with 1000 times dilution, and incubated at 37° C. for 1 hour. Then the membrane was washed 3 times with PBST. The immune complex was detected by electrochemiluminescence (ECL) according the instruction manual. The induced recombinant G protein was verified by Western Blot (WB) using a goat anti-RSV antibody as shown in the FIG. 1C. The results showed that both the RSV G protein in inclusion bodies and the RSV G protein in soluble form showed good antigenicity and can be recognized by anti-RSV antibodies.

C. Production and Purification of Recombinant G Protein from Inclusion Bodies

1) Acquisition of Primary Seed Liquid.

A single colony of BL21(DE3)/pET28a-noG was picked and incubated in 50 ml of LB medium supplemented with antibiotics, and shaken at 220 rpm for 8-10 hours at 37° C. to obtain a primary seed liquid.

2) Acquisition of Secondary Seed Liquid.

The primary seed liquid obtained in the step 1 was seeded into 500 ml of LB medium (with antibiotics) at a 5% of seeding ratio, and shaken at 220 rpm for 8-10 hours at 37° C. to obtain a secondary seed liquid.

3) Production of Recombinant RSV G Protein.

The secondary seed liquid obtained in step 2 is seeded into the fermenter at a seeding rate of 5%-10%. When $OD_{600nm}$≥3, the feeding was started; when $OD_{600nm}$≥18, the 1-5 mM of IPTG was added and the cultured temperature is 37° C. during the whole fermentation procedure. At the end of induction, the bacteria were collected by a centrifugation.

4) Extraction and Purification of Recombinant RSV G Protein

The fermented bacteria obtained in step 3 was resuspended in PBS at 1:10, crushed twice by high-pressure homogenizer (pressure=850-900 kg/cm2), then centrifuged at 10,000 rpm for 15 min and the inclusion body is stored at −20° C.

After the inclusion bodies were thawed, resuspended and washed 1-5 times with Buffer A (Buffer A: 50 mM Tris-HCl, 5 mM EDTA, 100 mM NaCl, pH 8.5) containing 1% Triton X-100 with the ratio at 1:20. The supernatant was discarded after centrifugation at 10,000 rpm for 15 min, and the precipitate was collected. The supernatant and the precipitate were detected by SDS PAGE.

2.5 g of washed inclusion bodies were then resuspended in Buffer B in a ratio at 1:10 (Buffer B formula: 8 M urea, 20 mM Tris-HCl, 5 mM EDTA, 100 mM NaCl, 10 mM DTT, pH 8.5). The denatured protein solution was obtained after the inclusion body was dissolved in Buffer B; 50 ml of the denatured protein solution was added to 950 ml of Buffer C at a rate of 5 ml/min under low-speed agitation (Buffer C Formulation: 700 mM urea, 20 mM Tris-HCl, 500 mM arginine, 1 mM cystamine dihydrochloride, 5 mM Cysteine, 15% glycerol, pH 9.0), stir (≤100 rpm) for 40 h at low temperature (2-8° C.).

The protein solution harvested from the preceding step was centrifuged at 16,000 rpm for 10 min at 2-8° C., and then the supernatant was transferred into a (MW8000-14000) dialysis bag for dialysis with refolding solution: dialysate (V:V) at 1:10. Dialysis at low temperature (2-8° C.) for 24 h with change the buffer every 12 hours during the dialysate procedure was then performed.

Afterwards, centrifugation with 16,000 rpm for 10 min at 2-8° C. was performed, and then the supernatant was collected in the dialysis bag for SDS-PAGE detection and the G protein (35 kDa) was visible.

The supernatant harvested at the preceding step was transferred into a (MW8000-14000) dialysis bag, put into 30% PEG8000 solution, and concentrated at 2-8° C. for 5-8 hours until the concentrated volume reached to ⅓~⅕ of the original volume. Then, centrifugation with 12,000 rpm for 10 min at 2-8° C. was performed. The supernatant was collected, and 1-2% mannitol, 1-3% glucose, 5 mmol arginine (W/V) was added for dissolution. Aliquots were prepared with 5.0 ml/vial after being filtered with a 0.22 μm filter, and frozen at −80° C. Lyophilized purified recombinant G protein with water content ≤1.0% was sealed in the vial.

D. Extraction and Purification of Soluble Recombinant RSV G Protein

1) Acquisition of Primary Seed Liquid

A single colony of BL21(DE3)/pET28a-noG was picked and incubated in 50 ml of LB medium supplemented with antibiotics, and shaken at 220 rpm for 8-10 hours at 37° C. to obtain a primary seed liquid.

2) Acquisition of Secondary Seed Liquid

The primary seed liquid obtained in the step 1 was seeded into 500 ml of LB medium (with antibiotics) at a 5% of seeding ratio, and shaken at 220 rpm for 8-10 hours at 37° C. to obtain a secondary seed liquid.

3) Acquisition of Recombinant G Protein

The secondary seed liquid obtained in step 2 was seeded into a fermenter at a seeding ratio of 5%-10%. When $OD_{600nm}$≥3, the feeding was started; when $OD_{600nm}$≥18, the 1-5 mM of IPTG was added and the cultured temperature was set at 30° C. during the whole fermentation procedure. At the end of induction, the bacteria were collected by centrifugation and pellets were frozen at −20° C.

4) Extraction and Purification of Recombinant G Protein

The bacteria pellets obtained in step 3 were resuspended in PB buffer at pH 8.0 at a ratio of 1:10, processed twice or more through a high-pressure homogenizer, and the pressure was set at 850-900 kg/$cm^2$, and the supernatant was collected by centrifugation.

The supernatant was adjusted to pH 9.6, then heated at 50-75° C. for 30 min, cooled down before subjected into a centrifugation at 10,000 rpm for 20 min at 2-8° C. to allow the supernatant being collected. The supernatant was then uploaded onto an anionic column chromatography (Q Bestarose High Performance or Capto™ Q) at 10° C. or lower to collect pass through. The pH of filtrated solution was adjusted to 8.5 and centrifuged at 10,000 rpm for 20 min at 2-8° C. The supernatant was collected.

Next, the supernatant thus collected was uploaded onto cationic column chromatography (CM SFF) with pH 8.0-8.6 (e.g., pH 8.5) at 2-8° C. (e.g., at 4° C.), washed with Triton X-114, pure water, and 200 mM of NaCl. The recombinant G protein fraction was eluted by a 240 mM of NaCl elution buffer.

A final concentration of PB 10 mM, NaCl 150 mM, polyethylene glycol (15)-hydroxystearate (Kolliphor® HS 15) at 0.1-1%, mannitol 1-5% was added into the eluted recombinant G protein for the lyophilization. After the lyophilization process, the sample was dried, capped, and covered with an aluminum cap to achieve a RSV recombinant G protein 5 product.

Example 2: Detection of RSV Recombinant G Protein with Anti-RSV Serum

Methods

A. Anti-Serum from Individuals Infected with RSV in Recovery Phase

Serum samples were collected from human subjects infected with RSV and in recovery stages. The recombinant RSV G protein prepared according to Example 1, including those in the inclusion bodies and those in soluble form, were tested to examine their binding activity to the anti-RSV serum.

B. Examining Binding Activity of Recombinant RSV G Proteins to Human Anti-RSV Serum 1) Serum Separation The collected blood samples were placed in a 37° C. for 2 hours, and centrifuged at 3000 rpm for 10 minutes after agglutination. The anti-serum samples were carefully aspirated and stored at −80° C.

2) Detection of Binding Activity

Recombinant RSV G protein in soluble form or in inclusion bodies were diluted to reach a final concentration of 2 μg/ml, coated onto a 96-well ELISA plate with 100 μl per well, and incubated at 37° C. for 2 hours or at 2-8° C. overnight. The plates were washed 3 times with PBST, followed by incubation with a PBST blocking buffer supplemented with 5% skim milk powder at 37° C. for 1 hour.

The anti-RSV serum was diluted with PBST supplemented with 2% skim milk powder at 2-fold serial dilutions starting at 1:200 to 1:1600 dilutions. The serially diluted anti-sera were added to 96-well ELISA plate (100 μl per well) and incubated at 37° C. for 1 hour followed by 5 washes with PBST.

HRP-labeled goat anti-human IgG at 100 μl of 1:4000 dilution was added to each well, incubated at 37° C. for 1 hour, then washed with PBST for 6 times. 100 μl TMB substrate were then added to each well and incubated at 37° C. for 15 minutes. The reaction was terminated by adding 50 μl of 0.2 mol/L sulfuric acid per well. The optical density value per well was measured at $OD_{450nm}/OD_{620nm}$ with an ELISA plate reader.

Results

As shown in FIGS. 2A-2C, the recombinant RSV G protein, either in soluble form or in inclusion bodies, was able to bind to anti-RSV-positive sera collected from three individuals. Soluble RSV G protein showed higher binding activity to the anti-RSV sera as compared with the RSV G protein in inclusion bodies.

These results demonstrate that the recombinant RSV G protein expressed in E. coli in soluble form has a higher binding activity to human anti-RSV sera relative to its inclusion body counterpart, suggesting that the soluble RSV G protein may be more suitable for use in development of RSV vaccine.

Example 3. Preparation of Aqueous Cyclosporine Solution

Cyclosporine A (CsA) is a poorly soluble compound and is commonly dissolved in propylene glycol at 1 mg/ml as a stocking solution, which can be diluted with PBS, if needed. This example aims at resolving the poor solubility issue with CsA. It provides an efficient method for producing aqueous solutions of CsA, which can be used to dissolve lyophilized recombinant RSV G proteins as disclosed herein to produce immune compositions comprising RSV G protein and CsA (G+CsA).

To produce an aqueous solution of CsA, Cyclosporin A was first dissolved in Kolliphor® HS 15 (polyethylene glycol (15)-hydroxystearate), a solubilizer, at 40-70° C. at a weight ratio of 1:5-50 (e.g., 1:20-50). Next, pure water of 40-70° C. and PB buffer were added to the CsA/Kolliphor® HS 15 solution to produce a clear aqueous solution. This aqueous solution can be used to dissolve lyophilized recombinant G proteins such as those described herein to yield the G+CsA vaccine composition. Compared with the recombinant RSV G protein dissolved in the propylene-based solution system (organic), the Kolliphor® HS 15-based aqueous solution system is equally effective in eliciting immune responses when used for making G+CsA vaccine compositions. The preparation of Kolliphor® HS 15 (polyethylene glycol (15)-hydroxystearate) based CsA solution is not required for the explosion-proof container or equipment, which is required for preparation of propylene glycol based CsA solutions.

Example 4: Hemolytic Assays for Different Formulations Containing Recombinant RSV G Proteins Non-ideal components used in formulations could result in hemolysis and local reactions for vaccines. To avoid such unwanted side-effects, different formulations of the recombinant G protein were tested in the hemolytic experiments as listed below:
Formulation groups:
0, Blank: 500 µl PBS+500 µl PBS
1, Negative Control: 500 µl 2% red blood cell (RBC) suspension+500 µl PBS
2, Kolliphor® HS 15 (polyethylene glycol (15)-hydroxystearate) Only: 500 µl 2% red blood cell suspension+500 µl 1×Kolliphor® HS 15 (polyethylene glycol (15)-hydroxystearate)
3, CsA in Kolliphor® HS 15 (polyethylene glycol (15)-hydroxystearate): 500 µl 2% red blood cell suspension+1×CsA in Kolliphor® HS 15 (polyethylene glycol (15)-hydroxystearate)
4, Propylene Only: 500 µl 2% red blood cell suspension+500 µl propylene solvent (400 µl PBS+100 µl propylene)
5, CsA in Propylene: 500 µl 2% red blood cell suspension+500 µl CsA in propylene (400 µl CsA solution+100 µl propylene)
6, Positive Control: 500 µl 2% red blood cell suspension+500 µl water The above components in preparations were applied to detect erythrocyte sedimentation and co-incubation absorbance, respectively.

Mouse blood was collected and added with 800 µl of 15 mg/ml of EDTA to prevent the coagulation. It was centrifuged at 1,500 rpm for 15 min followed by discarding of the supernatant. The pellet was resuspended into 1 ml PBS, and centrifugated at 1,500 rpm for 15 min. The procedure was repeated for approximately 2 or 3 times until the supernatant became clear. The pellet containing red blood cells was resuspended with PBS at 1:10 to get 10% of red cell suspension after discarding supernatant, then further diluted into 2% with PBS. Five hundred microliters of 2% red blood cell suspension were mixed with 500 µl of different formulations, respectively, for a period of 180 minutes at 37° C. The hemolysis was recorded by a camera from the beginning to the end. After that, sample was centrifuged at 1,500 rpm for 2 min, the absorbance of supernatant was measured at $OD_{405nm}$ and the results were statistically analyzed.

Figure 3A:
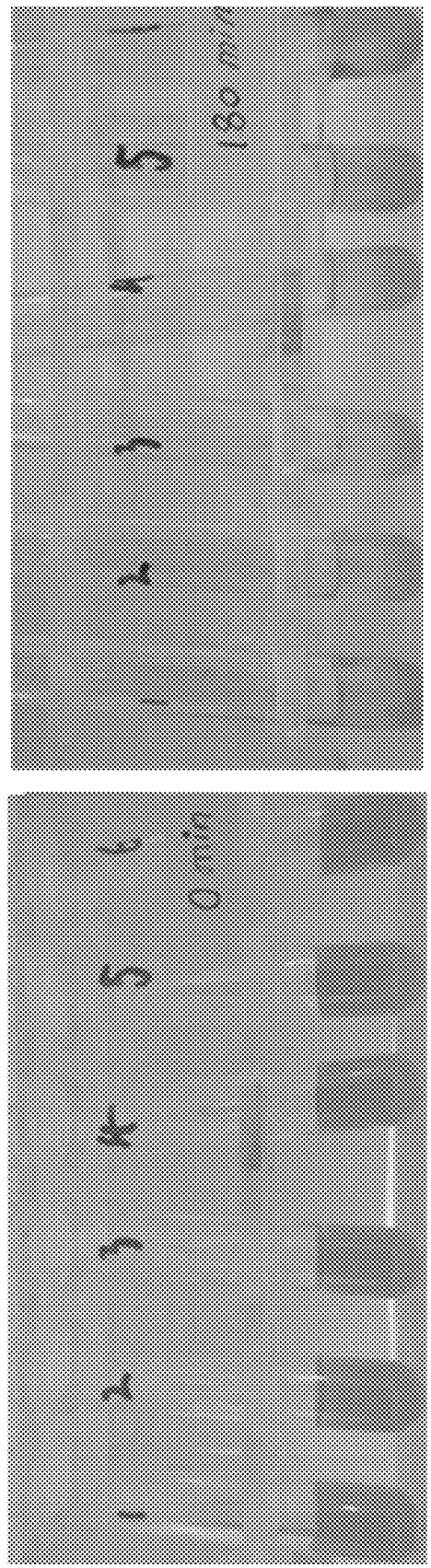
Figure 3B:
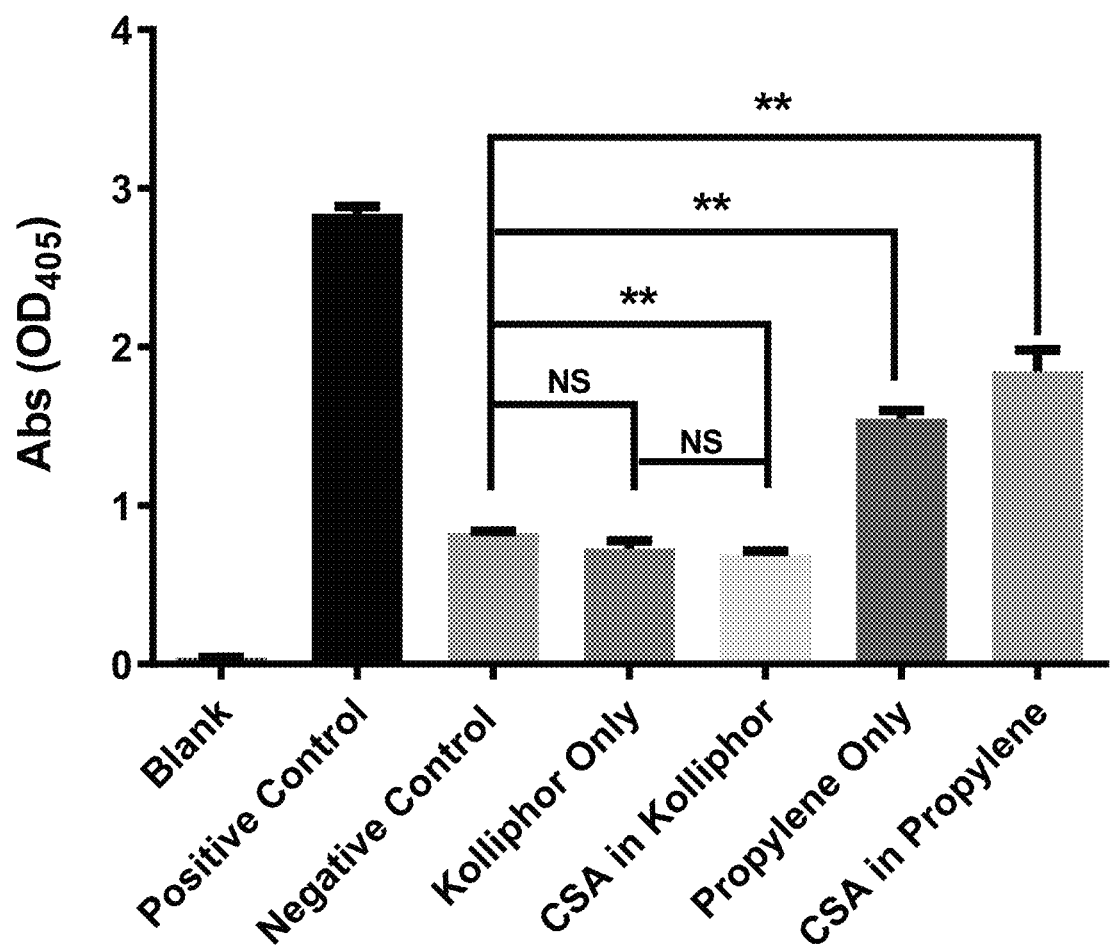

As shown in FIG. 3A, no hemolysis was observed with formulations containing Kolliphor® HS 15 (polyethylene glycol (15)-hydroxystearate) or CsA in Kolliphor® HS 15 (polyethylene glycol (15)-hydroxystearate). Various degrees of hemolysis occurred with formulations containing propylene glycol or CsA in propylene glycol (FIG. 3A). These results are consistent with those obtained by absorbance measurements of the supernatants after RBC incubation with different formulations (FIG. 3B). Thus, Kolliphor® HS 15 (polyethylene glycol (15)-hydroxystearate) can be a suitable component for use in making formulations comprising CsA.

Example 5: Local Skin Irritation Test of Different Formulations Containing Recombinant RSV G Protein Female BALB/c mice with age of 1 week, 6-8 weeks and 50 weeks after birth were purchased from Beijing Huafukang Bioscience Co. Inc. Each group contained 3 animals. Those animals were housed in a condition with 12 hr light cycle with sterile water and food.

One-week old female BALB/c mice were subcutaneously (SubQ) injected with G+CsA vaccines at day 0. Appearance observations and cytokine detection from injected skin area were performed three days after immunization.

The 6-8 weeks old female BALB/c mice were injected SubQ with G+CsA vaccines at day 0. Appearance observation and cytokine detection of local skin were performed on the injection site three days after the immunization.

Figure 4:
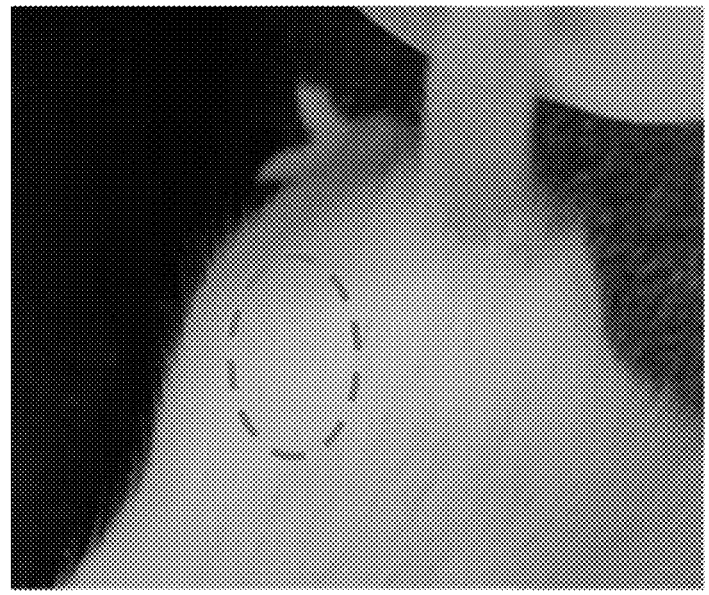
Figure 4:
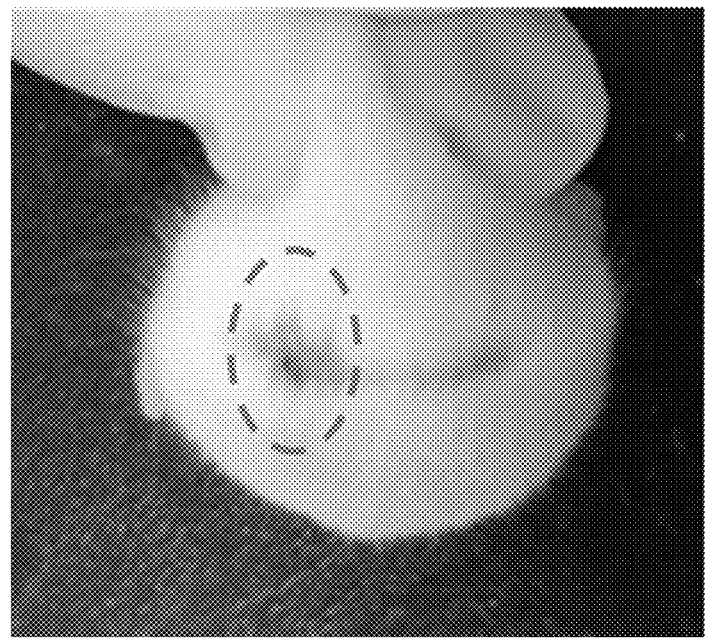

As shown in FIG. 4, the G+CsA vaccine in propylene glycol formulation can cause visible local redness inflammation and scarring at the injection site in both young and adult animals. However, there were no visible reactions with the G+CsA in Kolliphor® HS (polyethylene glycol (15)-hydroxystearate) formulated group (FIG. 4). Meanwhile, local cytokine production results showed that the G+CsA in propylene group had high cell damage-related pro-inflammatory cytokine at injection sites whereas the G+CsA in Kolliphor® HS (polyethylene glycol (15)-hydroxystearate) formulation group did not. These results were consistent with the observed results in Example 3.

In summary, these results indicate that the CsA in propylene glycol-formulation can cause high degrees of side effects whereas the CsA in Kolliphor® HS (polyethylene glycol (15)-hydroxystearate) formulation did not. Thus, the CsA in Kolliphor® HS (polyethylene glycol (15)-hydroxystearate) may be a component to develop G+CsA vaccines.

Example 6: The Role of CsA as an Immune Regulator in RSV Immune Compositions A. Dose Dependence of CsA in RSV Vaccine Materials: Female BALB/C mice with clean level, aged 6-8 weeks, were purchased from Beijing Huafukang Bioscience Co. Inc. Seven groups and 5 mice per group were set and housed in 12 hr light cycle with sterilized water and food.

Methods: according to different weight ratio of CsA and recombinant G protein, seven groups were divided as shown in Table 1.

TABLE 1

Recombinant RSV G protein and CsA in each group

| GROUPS | CSA(μg /MOUSE) | RECOMBINANT G PROTEIN(μg /MOUSE) |
|---|---|---|
| 1 | 0 | 10 |
| 2 | 1 | 10 |
| 3 | 2 | 10 |
| 4 | 4 | 10 |
| 5 | 6 | 10 |
| 6 | 8 | 10 |
| 7 | 10 | 10 |

Note:
Various concentrations of CsA were used to dissolve lyophilized recombinant G protein before subQ immunization at days 0 and 14. Peripheral blood was collected at day 28 for antibody detection.

Anti-RSV IgG Titer Detection Procedure Using ELISA was Performed as Follows:

1) Orbital blood was collected.
2) The collected blood was placed in a 37° C. incubator for 2 hours. After agglutination, it was transferred to a centrifuge and centrifuged at 3000 rpm for 10 minutes. After thoroughly separating the serum, the serum was carefully aspirated and stored at −80° C.
3) 96-well plates were coated with 100 μl recombinant G protein at concentration of 2 μg/ml (50 mM carbonate-bicarbonate buffer, pH 9.6) and incubated at 2-8° C. overnight.
4) Plates were washed 3 times with PBST. 5% skim milk powder (PBST) was added, and plates were incubated at 37° C. for 2 hours.
5) The solution was discarded, and plates were washed 3 times with PBST. Then, the plates were incubated with serially diluted (2-fold) serums for 1.5 h at 37° C.
6) The diluted serums were discarded, and the plate was washed 6 times with PBST. 100 μl of HRP-labeled goat anti-human IgG diluted 4000-fold with 2% skim milk powder (PBST) was added to each well, and allowed to incubate at 37° C. for 1 hour, and then washed with PBST 6 times.
7) 100 μl of TMB substrate was added to each well, and plates were incubated at 37° C. for 15 minutes with avoiding the light. The reaction was terminated by adding 50 μl of 0.2 mol/L sulfuric acid per well.
8) The optical density value per well was measured at $OD_{450nm}$ and $OD_{620nm}$.

Neutralizing Antibody Assays were Performed as Follows:

1) Approximately $5\times10^3$ HEp-2 cells in 100 μl DMEM supplemented with 2% FBS were added to each well of a 96-well microtiter plate.
2) Serum was heat inactivated at 56° C. for 30 min and serially diluted (2-fold) in a total of 100 μl PBS.
3) Then 75 μl diluted sera were incubated with 25 μl $3\times10^3TCID_{50}$ of virus for 2 h at 2-8° C.
4) The virus and serum mixture were added to the appropriate wells and incubated for 3 days in a 5% $CO_2$ incubator at 37° C.
5) Plates were then washed three times with 0.05% Tween® 20 in PBS and fixed with 80% cold acetone in PBS followed by blocking with 3% blocking buffer.
6) Goat anti-RSV antibody (Meridian, Me., USA) diluted 4000-fold with 2% skim milk powder (PBST) was added to the appropriate wells and incubated for 1 hour at 37° C.
7) After three washings, bovine anti-goat IgG-HRP (Santa Cruz, Calif., USA) diluted 6000-fold with 2% skim milk powder (PBST) was added, the enzymatic reaction was developed and ODs were measured at 450 nm and 620 nm.
8) The neutralization titer was calculated from the average OD of the wells by extrapolating the inverse of the serum dilution that resulted in 50% reduction of RSV activity.

Results: When the concentration of CsA increased to 10 μg/mouse, the serum IgG titer (FIG. 5A) and neutralization antibody titer (FIG. 5B) of mice in the G+CsA immunized group and the G-immunized group were significantly increased. Additionally, the level of antibodies decreased with the descending dose of CsA. The positive relation between CsA dosage and antibody titer in humoral response showed a dose dependent effect of CsA as an adjuvant in the RSV vaccine.

Conclusion: A dose-dependent immune reaction of CsA indicates that 10 μg/mouse CsA with 10 μg/mouse recombinant G protein may be used for further immunization.

B. Effects of CsA on IgG Subtypes in Vaccinated Mice

Materials: Female BALB/C mice aged 6-8 weeks were purchased from Beijing Huafukang Bioscience Co. Inc. Five mice in each group were set and housed in 12 hr light cycled room with sterilized water and food. The RSV vaccine was prepared as the same as mentioned above.

Methods: Mice were immunized with 10 μg of CsA and 10 μg of recombinant G protein subQ at days 0 and 14, the control group were immunized with same amount of recombinant G protein only. Using ELISA methods, peripheral blood was collected at day 28 for IgG subtypes detection, including IgG1, IgG2a, IgG2b and IgG3, and examined by ELISA for their titers of four subtypes. ELISA assay procedures were used as the same as described in the above experiment.

Results: The treatment group showed significant higher titer of IgG1, IgG2a, IgG2b compared to the control group, while both groups showed no significant different titer of IgG3. FIG. 5C Conclusion: CsA as an adjuvant to the recombinant G protein vaccine enhanced the production of three subtype's antibodies, IgG1, IgG2a and IgG2b, but showed no significant effect on the IgG3.

C. Effects of CsA on Germinal Central (GC) B Cells and Plasma B Cells

Materials: Female BALB/C mice with clean level, aged 6-8 weeks, were purchased from Beijing Huafukang Bioscience Co. Inc. Four groups and 5 mice in each group were set. Sterilized water and food were used during the experiment, and the photoperiod was 12 hours. Methods: Mice were immunized with 10 μg/mouse of CsA and 10 μg/mouse of recombinant G protein subcutaneously at day 0 and day 14 as treatment group, the control group were immunized with same amount of recombinant G protein, CsA or PBS alone. At day 28, recombinant G protein was intramuscularly injected to stimulate the body as a simulation of RSV infection, and the serum were collected from peripheral blood for IgG titer evaluation. At day 32, spleen and drain lymph nodes near the injection site were isolated for flow cytometry of germinal central (GC) B cells and plasma cells. The cell proportion were analyzed.

1) Single cell suspension was prepared as follows:
The mice were anaesthetized before euthanizing. The spleen and lymph nodes were isolated carefully under sterilized conditions before grinding into single cell solution with RPMI 1640. The single cell solution was centrifuged with 1500 rpm for 3 mins, the supernatant was discarded. Red blood cell lyses buffer was used to resuspend the pellet with a 750 μl/spleen volume. After 2 mins resuspending, 500 μl Fetal bovine serum were added to terminate the red blood cell lysis, then centrifuged with 1500 rpm for 3 mins, the supernatant was discarded. Using RPMI 1640 with 10% fetal bovine serum (FBS) to resuspend the pellet, the solution then was centrifuged with 1500 rpm for 3 mins, and the supernatant was discarded. The pellet was resuspended with RPMI1640 containing 10% FBS as single cell suspension for further staining.

2) Flow cytometry assay was performed as follows:
Single cell suspension was transferred into 96-well rounded plate with a concentration of 1 000 000 cell/well. The plate then was centrifuged with 1500 rpm for 3 mins, discard the supernatant. 50 μl/well diluted fluorescent antibody were added to gently resuspend the cell pellet according to the instructions. Briefly, samples were stained with Fixable Viability Dye eFluor™ 780 (eBioscience) to remove dead cells before antibody staining. Cells were stained with the following surface antibodies: B220 APC (eBioscience), GL-7 PE (eBioscience). After 30 mins under 4 degree centigrade avoiding light, 200 μl/well PBS was added to terminate the staining procedure. The plate then was centrifuged with 1500 rpm for 3 mins, discard the supernatant. Using 200 μl/well PBS to resuspend the pellet, the plate then was centrifuged with 1500 rpm for 3 mins, discard the supernatant. Resuspend with 150 μl/well PBS for flowcytometry detection. Herein, GC B cells were defined as B200+GL7+ cells, plasma B cells were defined as B220+CD138+ cells.

Figure 5A:
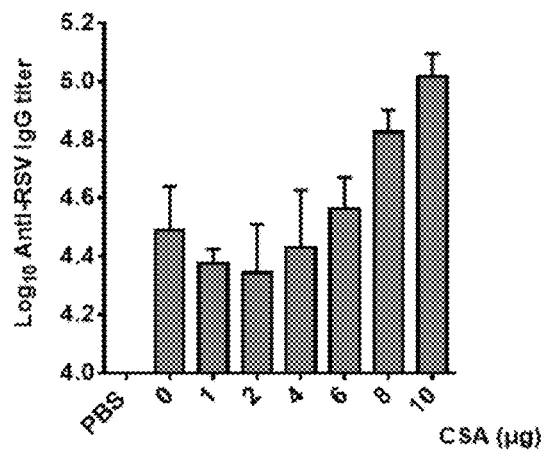
Figure 5B:
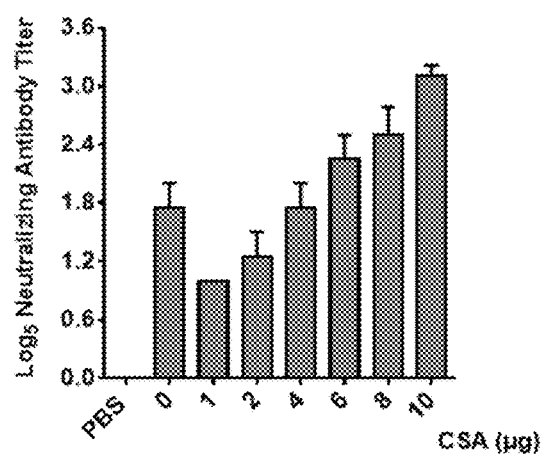
Figure 5C:
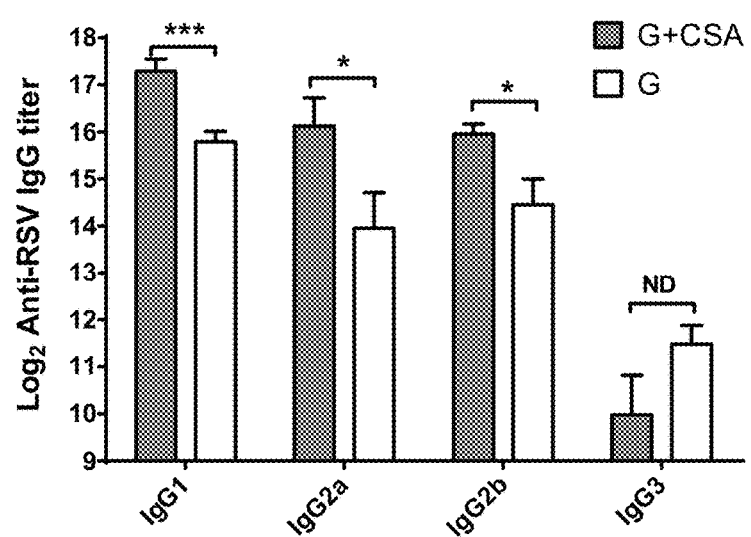
Figure 5D:
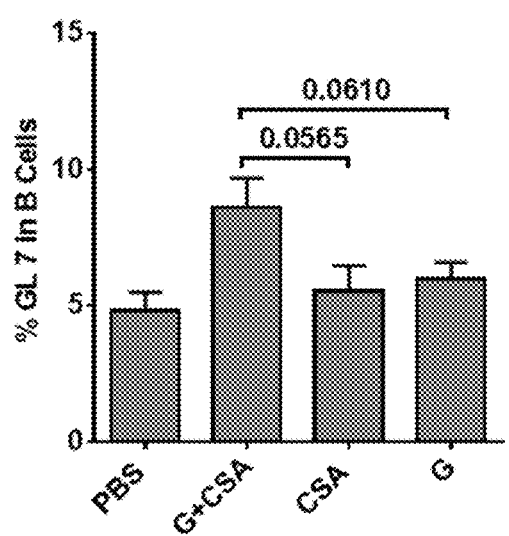
Figure 5E:
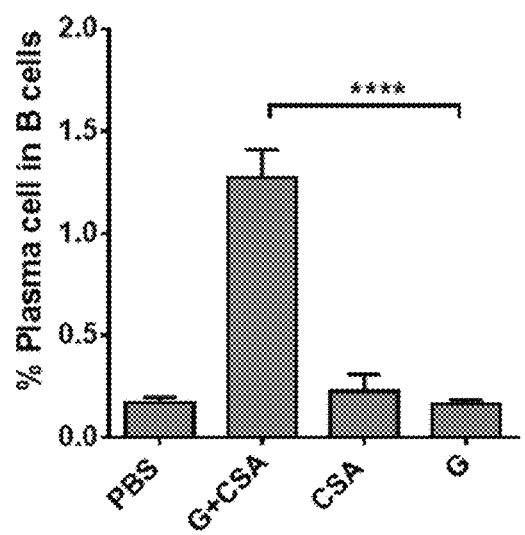

Results: The ratio of GC B cells in lymph nodes was significantly higher in G+CsA immunized group compared with that in the G-immunized group. FIG. 5D and FIG. 5E. In spleen, the plasma B cells also showed a significant higher ratio in G+CsA immunized group compared with all other groups. While in lymph nodes, no significant difference was observed between G+CsA immunized group and G-immunized group. Both G+CsA immunized group and G-immunized group showed significant higher ratio of plasma B cell compared to CsA-immunized group and PBS group. Besides, after recombinant G protein stimulation, G+CsA immunized group manifest a significant higher titer of IgG than before stimulation, and also higher than G-immunized group after stimulation.

Conclusion: CsA promotes the generation of GC B cells in spleen and lymph nodes as an adjuvant, and helps induce more plasma cells in spleen after vaccination with recombinant G protein. The decrease of plasma cells in lymph node from G+CsA immunized group may relate to its migration to spleen.

D. Recombinant RSV G Protein+CsA Immune Composition Prevents RSV Reinfection in Mice Materials: Female BALB/C mice with clean level, aged 6-8 weeks, were purchased from Beijing Huafukang Bioscience Co. Inc. Four groups and 5 mice in each group were set. Sterilized water and food were used during the experiment, and the photoperiod was 12 hours.

Methods: According to the Table 2, the mice were separated into 5 groups, with or without CsA and recombinant G protein vaccination at day −28 and day −14, then the mice were infected intranasally (i.n.) with or without $5 \times 10^7$ PFU of RSV A2 in 50 μl volume under anesthesia at day 0, day 13 and day 26. Constantly weight change and mice lung tissue immune histology at day 40 were taken to evaluate the protection effects of vaccine on re-infection RSV mice model.

TABLE 2

CsA and recombinant G protein in each group.

| Groups | CsA (μg/mouse) | recombinant G protein (μg/mouse) | RSV challenge (i.n.) |
|---|---|---|---|
| 1 | 0 | 0 | 0 |
| 2 | 0 | 0 | 1 |
| 3 | 0 | 10 | 1 |
| 4 | 10 | 0 | 1 |
| 5 | 10 | 10 | 1 |

Figure 5F:
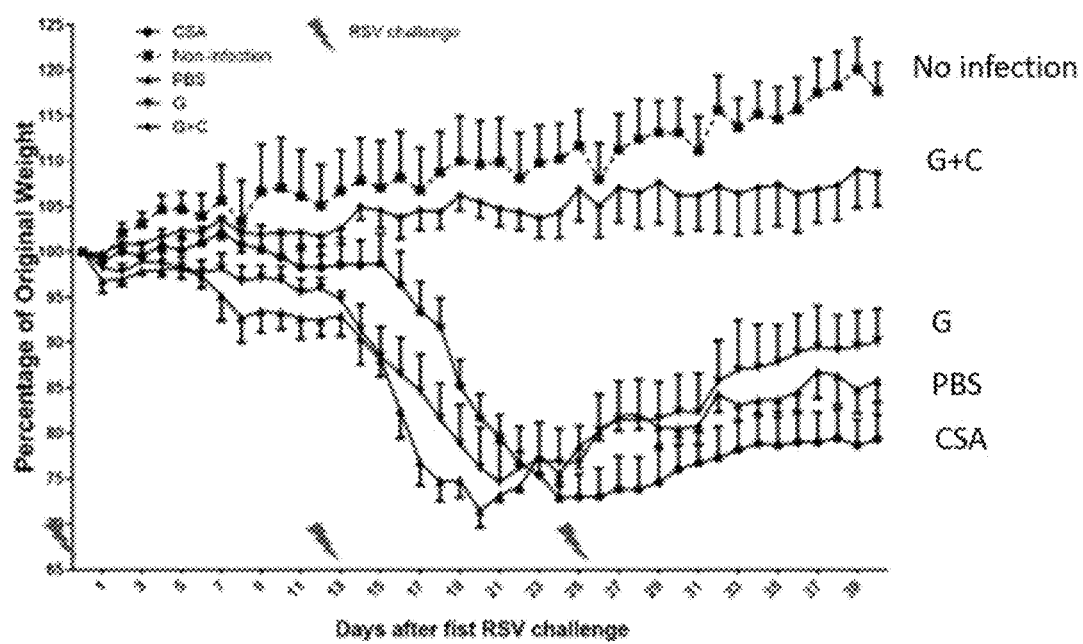

Results: Mice in G+CsA-immunized group showed the mildest weight fluctuation, similar to the mice in PBS-immunized group, while in G-immunized group and CsA-immunized group, the mice showed significant weight loss after RSV infection. FIG. 5F. At day 40, the HE staining of lung tissue showed that G+CsA immunized mice remained intact morphology manifestation, significantly less infiltrated with inflammatory cells, similar to the uninfected group. The lung tissue in the G-immunized alone mice and CsA-immunized alone mice were revealed a significantly areas of inflammation with massive cell infiltration and morphological lesions with undistinguished bronchia and pulmonary alveoli structures.

Conclusions: According to the weight change and lung tissue histology staining after RSV challenge, G+CsA vaccination can rescue drastic weight loss and prevents lung tissue damage from virus infection. Furthermore, the vaccine can effectively protect mice from repeated RSV exposure.

Example 7. CsA Promotes Humoral Immunity, Treg Cells, and Tfh Cells

A. The Effect of CsA on Promoting Humoral Immunity

Materials: Female BALB/C mice with clean level, aged 6-8 weeks, were purchased from Beijing Huafukang Bioscience Co. Inc. Four groups and 5 mice in each group were set. Sterilized water and food were used during the experiment, and the photoperiod was 12 hours.

Methods: At day 0, 14, the mice were immunized subcutaneously on the back with recombinant G protein (10 μg/mouse) and CsA (10 μg/mouse), the control groups were immunized with recombinant G protein (10 μg/mouse), CsA (10 μg/mouse) or PBS only. At day 28, all mice were infected with RSV. 4 days later, spleen and lymph node were isolated for the detection of Tfh and Treg proportion and cytokine IL-21 from Tfh. Procedure of single cell suspension from spleen and lymph node were described above. Flow cytometry staining of Tfh cells and Treg cells assay were performed as follows:
1) Single cell suspensions were added to the 96-well rounded plate with a concentration of 1 000 000 cells/well. Centrifuge the plate with 1500 rpm for 3 mins, and discard the supernatant.
2) Dilute the surface fluorescent antibody according to the instructions with staining buffer (PBS containing 2% FBS). Resuspend the pellet with diluted staining buffer with 50 μl/well gently. Stain for 30 mins at 2-8° C. away from light.
3) Add 200 μl/well PBS to terminate the staining procedure. Centrifuge the plate with 1500 rpm for 3 mins, discard the supernatant. Resuspend with 200 μl/well PBS, then centrifuge the plate with 1500 rpm for 3 mins, discard the supernatant.
4) Resuspend the pellet with 200 μl/well fixation-permeabilization buffer according to the instructions, fixation for 50 mins at 2-8° C. away from light.
5) Centrifuged with 1500 rpm for 3 mins, discard the supernatant. Add permeabilization buffer 200 μl/well to wash the pellet, discard the supernatant after centrifugation.
6) Resuspend the plate with 50 μl/well diluted intracellular antibody in permeabilization buffer. Shake for 60 mins at room temperature.
7) Add 200 μl/well PBS to terminate the staining procedure. Centrifuge the plate with 1500 rpm for 3 mins, discard the supernatant. Resuspend with 200 μl/well PBS, then centrifuge the plate with 1500 rpm for 3 mins, discard the supernatant. Resuspend the pellet with 150 μl/well PBS for flow cytometer reading.

Figure 6A:
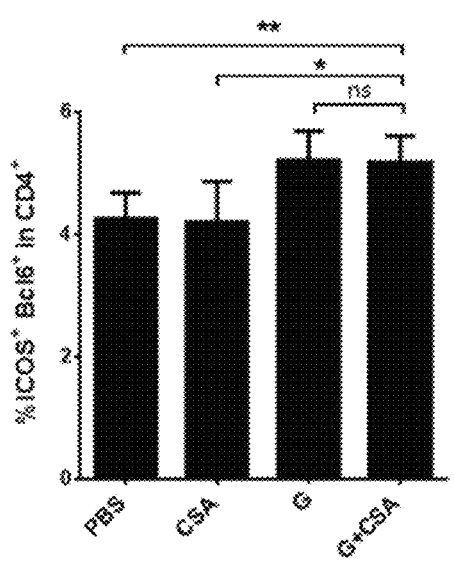
Figure 6B:
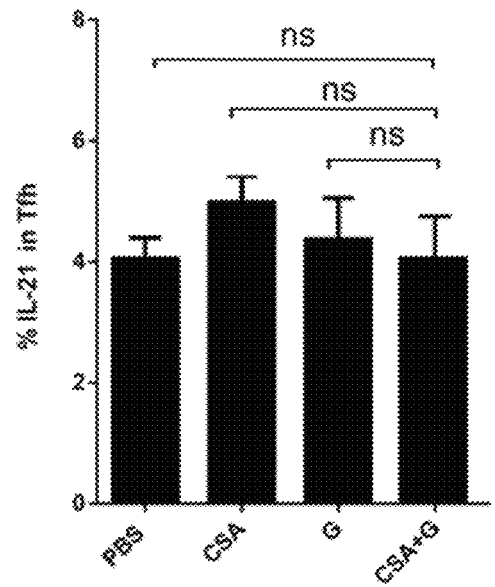

Results: The percentage of Tfh cells (FIG. 6B) in the spleen and lymph nodes of the G+CsA immunized group was not significantly different from that of the G-immunized group. The results of the Tfh functional cytokine IL-21 showed that there was still no difference between the two groups of mice.

Compared with PBS group, G+CsA immunized mice and G-immunized mice showed higher Tfh proportion. This result indicated that both the vaccination activates a certain amount of Tfh cells, assisting the antibody production to some extent. Since there was no statistically significant difference in the number of Tfh cells between the two groups of mice, Tfh cells were unlikely to be the cause of the difference in antibody levels. However, the number of Treg cells (FIG. 6A) in the spleen and lymph nodes of mice immunized with G+CsA was significantly higher than that of mice immunized with recombinant G protein alone.

B. Effects of Treg Cell Knockout on Vaccine-Induced Humoral Immunity

Materials: FoxP3-DTR-eGFP transgene female mice, aged 6-8 weeks, were nurtured in house with a clean level. Four groups and 5 mice in each group were set. Sterilized water and food were used during the experiment, and the photoperiod was 12 hours.

Methods: groups were set according to Table 3, DT were injected peritoneally before each vaccination, i.e. DT injection at day −1, −2, 12, 13 and vaccination at day 0, 14. Peripheral blood was collected at day 28. Then the serum was isolated for anti-RSV IgG titration, using ELISA method described herein.

TABLE 3

Recombinant G protein and CsA in each group.

| Groups | recombinant G protein + CsA | DT |
|---|---|---|
| 1 | 10 μg/mouse + 10 μg/mouse | 1 |
| 2 | 10 μg/mouse + 10 μg/mouse | 0 |
| 3 | 0 μg/mouse + 10 μg/mouse | 1 |
| 4 | 0 μg/mouse + 10 μg/mouse | 0 |

Figure 6C:
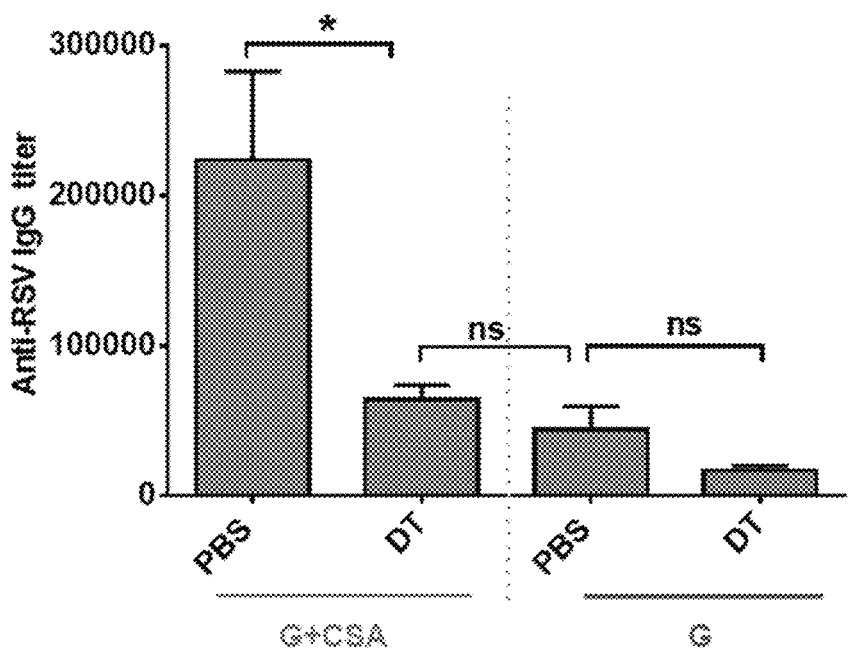

Results: After knocking out Treg cells, the antibody level of mice immunized with RSV G was almost unaffected and at a very low level. FIG. 6C. The IgG titration in mice immunized with G+CsA significantly reduced after Treg cells were knocked out, showing similar level to mice immunized with recombinant G protein only.

Conclusions: Treg cells did not play a role in humoral immunity in mice immunized with recombinant G protein alone. However, it significantly decreases the adjuvant effect of CsA in mice vaccinated with recombinant G protein+CsA.

C. Effects of Recombinant G Protein+CsA Induced Treg on Humoral Immunity In Vivo Materials: FoxP3-DTR-eGFP transgene female mice, aged 6-8 weeks, were nurtured in house with a clean level. Five groups and 5 mice in each group were set. Sterilized water and food were used during the experiment, and the photoperiod was 12 hours Methods: groups were set according to Table 4. Mice were immunized on day 0, 14, and infected with RSV at day 28. At day 32, Treg cells were isolated from mice vaccinated with recombinant G protein+CsA and recombinant G protein only by flow sorting. Then the two groups cell were transferred the other two groups of mice immunized with recombinant G protein on days 7 and 21. At day 31 and day 39, peripheral blood of receptor mice was collected for anti-IgG titration detection.

TABLE 4

Vaccination groups

| Groups | | recombinant G protein + CsA | Vaccination | Source of Treg |
|---|---|---|---|---|
| 1 | Treg donordonor | 10 ug/mouse + 10 ug/mouse | Day 0, 14 | — |
| 2 | Treg donor | 0 ug/mouse + 10 ug/mouse | Day 0, 14 | — |
| 3 | Treg receiver | 0 ug/mouse + 10 ug/mouse | Day 7, 21 | Group 1 |
| 4 | Treg receive | 0 ug/mouse + 10 ug/mouse | Day 7, 21 | Group 2 |
| 5 | Control | 0 ug/mouse + 10 ug/mouse | Day 7, 21 | — |

Conclusions: Neither the increase of Tfh amount nor the activation of Tfh cells caused the increasing antibody in mice vaccinated with G+CsA. G+CsA immunization can elicit Treg cells.

Procedure of Treg Sorting from FoxP3-DTR-eGFP Mice:

Single spleen cell suspension was prepared for flowcytometry staining with APC-CD4 fluorescence antibody. Then APC channel and GFP channel double positive cells were collected by flowcytometry sorting. After sorting, cells were centrifuged with 3000 rpm for 5 mins, resuspending for further transferring.

Figure 6D:
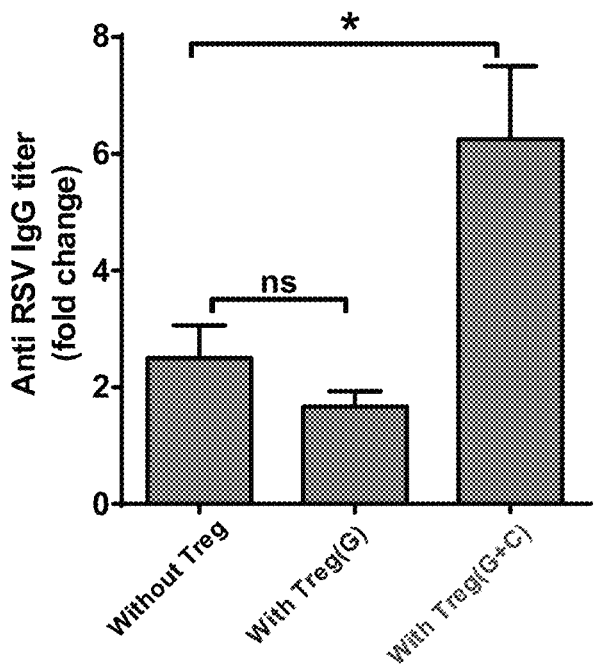

Results: IgG production was significantly elevated in G-immunized mice transferred with Treg cells from recombinant G protein+CsA vaccinated mice, compared to the control group. FIG. 6D. There was no difference observed in recombinant G protein vaccinated mice transferred with Treg cells from recombinant G protein vaccinated mice, compared to the control group.

Conclusions: Treg cells induced by recombinant G+CsA promote the production of specific antibodies in vivo.

D. Effects of G+CsA Induced Treg on Humoral Immunity In Vitro

Materials: FoxP3-DTR-eGFP transgene female mice, aged 6-8 weeks, were nurtured in house with a clean level. Four groups and 5 mice in each group were set. Sterilized water and food were used during the experiment, and the photoperiod was 12 hours.

Methods: groups were set according to Tables 5-6, and all mice were vaccinated at day 1, 14. At day 28, mice were infected with RSV. At day 32, mice were euthanized for cell sorting. Sorted B cells then were stained with eFluor™ 670 for further proliferation detection. Sorted conventional T cells and Treg cells were co-cultured with eFluor™ 670 stained B cells, with recombinant G protein added for stimulation. 3 days later, B cell proliferation was detected according to the fluorescence intensity of eFluor™ 670.

TABLE 5

Experimental groups

| recombinant G protein + CsA | RSV infection | Sorted cells |
|---|---|---|
| 10 μg/mouse + 10 μg/mouse | 1 | Treg |
| 0 μg/mouse + 10 μg/mouse | 1 | Treg |
| 10 μg/mouse + 10 μg/mouse | 1 | Tcon |
| 0 μg/mouse + 10 μg/mouse | 0 | B cells |

TABLE 6

Experimental groups

| Group | B cells | Treg (recombinant G protein + CsA) | Tcon (recombinant G protein + CsA) | Treg (recombinant G protein) | recombinant G protein stimulator | LPS |
|---|---|---|---|---|---|---|
| 1 | + | + | − | − | + | − |
| 2 | + | − | + | − | + | − |
| 3 | + | − | − | + | + | − |
| 4 | + | − | − | − | + | − |
| 5 | + | − | − | − | − | + |

Procedure of B Cell Sorting from FoxP3-DTR-eGFP Mice:

Single spleen cell suspension was prepared for flowcytometry staining with APC-B220 fluorescence antibody. Then APC channel and GFP channel double positive cells were collected by flowcytometry sorting. After sorting, cells were centrifuged with 3000 rpm for 5 mins, resuspending for further transferring.

Procedure of Staining B Cells with eFluor™ 670:
1) Prepare single cell suspension, wash 2 times with sterilized PBS.
2) Resuspend to 2 times of final concentration with PBS at room temperature.
3) Dilute cell proliferation dye eFluor™ 670 with PBS to a certain concentation, ready for use.
4) Mix solutions in 2) and 3) with 1:1 ratio, incubation for 10 mins at 37° C.
5) Add 4-5 times volume complete medium, incubation for 5 mins on ice to terminate the staining process.
6) Wash 3 times with PBS, resuspend for use.
7) Co-culture cells for 3 days, then detect the fluorescence intensity with flow-cytometer.

Figure 6E:
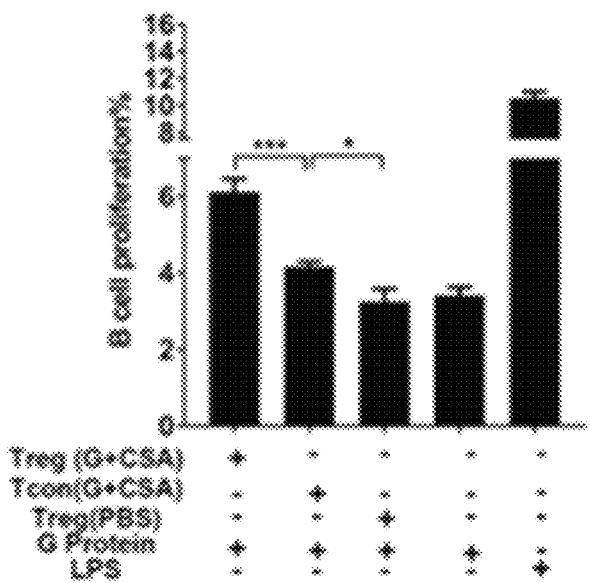

Results: As shown in FIG. 6E, Treg cells induced by G+CsA enhance the proliferation activity of specific B cell in vitro, significantly different when compared with conventional T cells (Table 6). Non-induced Treg showed no effect on B cell proliferation.

Conclusions: Treg cells induced by G+CsA promotes B cells differentiation through direct contact with B cells, and owns more potential than conventional T cells. The co-cultural experiment proved that a group of Treg cells induced by the addition of CsA as adjuvant could promote the production of B cell antibodies in vitro, and also proved that effector T cells (including Tfh cells) did not play a role in promoting humoral immunity in vitro.

E. Molecular Mechanism of G+CsA Induced Treg Affecting B Cell Functions

1) Functions of G+CsA on inducing Tregs

Materials: Female BALB/C mice, aged 6-8 weeks, were nurtured in house with a clean level. 5 mice in each group were set. Sterilized water and food were used during the experiment, and the photoperiod was 12 hours.

Methods:
(1) The mice were immunized with G+CsA and recombinant G protein alone at day 0, 14 respectively; the control group were immunized with PBS. Spleen and lymph node cells were isolated for flow cytometry staining at day 0, 3, 7, 10, 14 to evaluate the ICOS expression on Treg cells.
(2) The mice were immunized with G+CsA, recombinant G protein, or CsA only at day 0, and day 14; the control group were immunized with PBS. At day 28, all mice were infected with RSV. At day 32, CD40L and IL-10 of Treg cells in spleen were detected. Flow cytometry staining procedure was described as above.

Figure 7A:
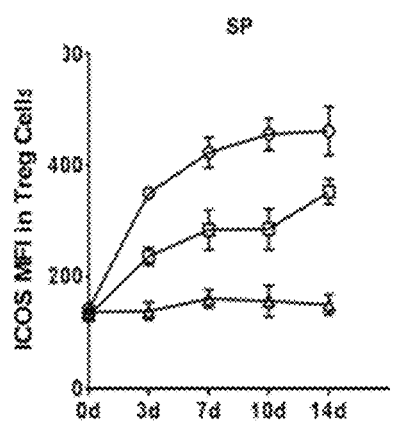
Figure 7B:
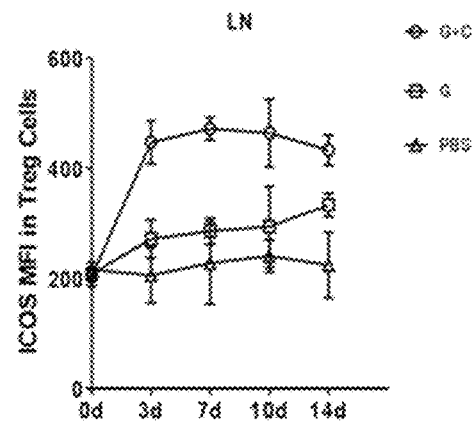
Figure 7C:
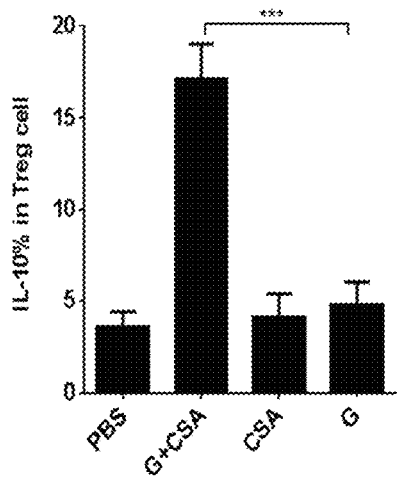
Figure 7D:
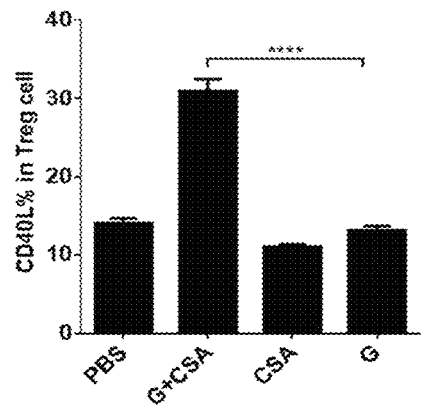

Results:
(1) At day 3, 7, 10, 14, Treg cells in mice immunized with recombinant G protein+CsA expressed significantly higher ICOS than Tregs in mice immunized with recombinant G protein only and PBS. FIGS. 7A and 7B.
(2) Treg cells in mice immunized with recombinant G protein+CsA expressed significantly higher CD40L and IL-10 than Tregs in mice immunized with recombinant G protein only and PBS. The percentage of IL-10/CD4 positive cells in groups treated with PBS (blank control), G+CSA, G alone, and CSA alone are 9.73%, 23.1%, 11.3%, and 7.14%, respectively. See also FIG. 7C. The percentages of CD40L+ cells in Treg cells of these groups are shown in FIG. 7D.

Conclusions: G+CsA induced Treg cells were activated earlier and expressed higher ICOS, CD40L, IL-10. Similar to Tfh cells, induced Treg cells have high expression of ICOS and CD40L, as well as IL-10, the main cytokine.

2) Effects of Blocking CD40L and IL-10 on Vaccine-Induced Antibody In Vivo

Materials: Female BALB/C mice, aged 6-8 weeks, were nurtured in house with a clean level. 5 mice in each group were set. Sterilized water and food were used during the experiment, and the photoperiod was 12 hours.

Methods: groups were set according to Table 7. All mice were vaccinated at day 0, 14 with recombinant G protein+CsA. Functional blocking antibodies were injected on the day before vaccination, isotype antibody were set as control group. At day 28, anti-RSV IgG were analyzed.

TABLE 7

Experimental groups

| Groups | recombinant G protein + CsA | Antibody blocking |
|---|---|---|
| 1 | 10 μg/mouse + 10 μg/mouse | Anti-IL-10 |
| 2 | 10 μg/mouse + 10 μg/mouse | Anti-CD40L |
| 3 | 10 μg/mouse + 10 μg/mouse | Isotype |

Figure 7E:
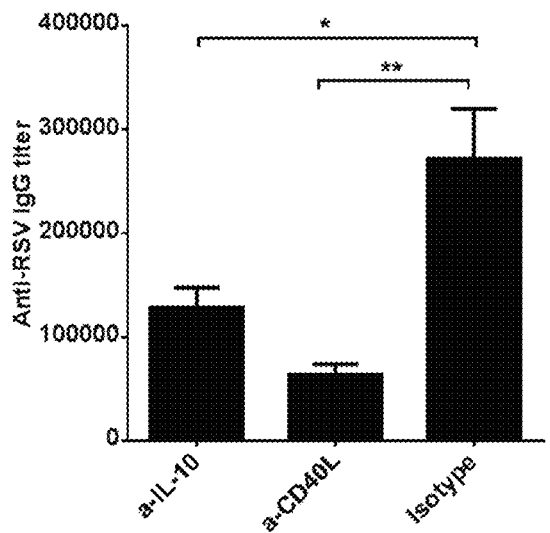

Results: Mice injected with functional blocking antibodies showed significantly inefficient antibody production, while mice treated with isotype antibody manifested an unaffected level. Statistically, there were significant differences in IgG levels between the isotype antibody blocking group and the other two functional antibody blocking groups. FIG. 7E.

Conclusions: Both CD40L and IL-10 played important roles in the progress of G+CsA induced Treg cells assisting B cell antibody production.

F: Identification of Assistant Role of G+CsA Induced Treg in B Cell Antibody Production Materials: FoxP3-DTR-eGFP transgene female mice, aged 6-8 weeks, were nurtured in house with a clean level. 5 mice in each group were set. Sterilized water and food were used during the experiment, and the photoperiod was 12 hours.

Methods: groups were set according to Tables 8-9.

For Treg acquiring, mice were vaccinated at day 0, 14, and infected with RSV at day 28. At day 32, all mice were euthanized for spleen Treg cells sorting.

For B cell acquiring, mice were immunized with recombinant G protein or PBS at day 0, 14. B cells and Tregs were sorted accordingly.

Sorted Treg cells and B cells were co-cultured with inactivated RSV as a stimulator. The concentrations of IL-10 and IgG in supernatant were detected 3 days later.

TABLE 8

Experimental groups

| recombinant G protein + CsA | RSV infection | sorting cells |
|---|---|---|
| 10 μg/mouse + 10 μg/mouse | 1 | Specific Treg |
| 10 μg/mouse + 10 μg/mouse | 1 | Non-specific Treg |
| 10 μg/mouse + 10 μg/mouse | 0 | Specific B cell |
| 10 μg/mouse + 10 μg/mouse | 0 | Non-specific B cell |

TABLE 9

Experimental groups

| Groups | Specific Treg | Non-specific Treg | Specific B cell | Non-specific B cell | Inactivated RSV |
|---|---|---|---|---|---|
| 1 | + | − | + | − | + |
| 2 | − | + | + | − | + |
| 3 | + | − | − | + | + |
| 4 | − | + | − | + | + |

Figure 7F:
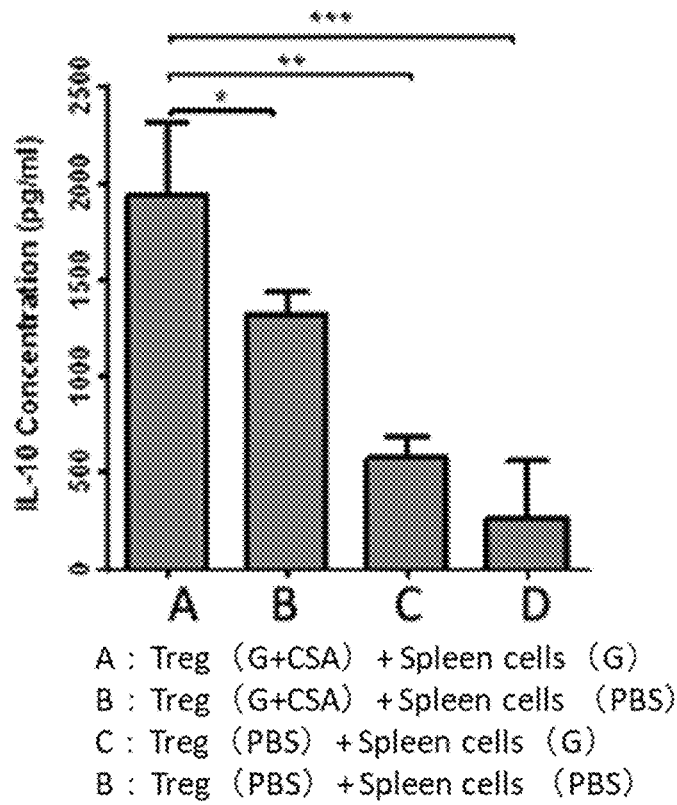

Results: IL-10 and IgG in the supernatant of co-culturing medium were tested and the result showed higher concentration observed after antigen specific Tregs co-cultured with B cells. In the supernatant of co-culturing specific Treg cells and non-specific B cells, only IL-10 showed a higher level. FIG. 7F. This indicated that specific antigen is required for specific Treg IL-10 production, while the production of IgG required specific antigen, antigen specific B cells and Treg cells. In the supernatant co-culturing non-specific Treg cells and non-specific B cells, neither the IL-10 production nor the IgG was enhanced, which means unlike specific Treg cells, non-specific Treg cells cannot secret IL-10, nor promote B cell functions. This indicates that only Treg cells induced by recombinant G protein+CsA can secrete IL-10 and play a role in promoting the function of B cells, while Treg cells without induction cannot perform similar biological functions.

Conclusions: In the vitro experiment, the specific production of total IgG and IL-10 demonstrated that iTreg cells induced by G+CsA, rather than conventional Treg cells, played an auxiliary role on B cells.

F. Identification of Assistant Role of G+CsA Induced Treg, Rather than Conventional T Cells, in B Cell Antibody Production Materials: FoxP3-DTR-eGFP transgene female mice, aged 6-8 weeks, were nurtured in house with a clean level. 5 mice in each group were set. Sterilized water and food were used during the experiment, and the photoperiod was 12 hours.

Methods: groups were set according to Tables 10-11. Functional blocking antibodies were injected on the day before vaccination, isotype antibody was set as control group.

For Treg and conventional T cells acquiring, all mice were vaccinated at day 0, 14 with G+CsA. At day 28, mice were infected with RSV. And at day 32, all mice were euthanized for sorting spleen Treg and conventional T cells.

For spleen cells acquiring, mice were immunized with recombinant G protein or PBS at day 0, 14. Spleens cells were isolated at day 32.

Sorted Treg cells or conventional T cells were co-cultured with spleen cells and inactivated RSV. 3 days later, ratio of plasma cells (B220+CD138+) in B cells (B220+) were detected by flowcytometry.

TABLE 10

Experimental groups.

| recombinant G protein + CsA | RSV infection | sorting cells |
|---|---|---|
| 10 μg/mouse + 10 μg/mouse | 1 | Specific Treg |
| 10 μg/mouse + 10 μg/mouse | 1 | Specific Tcon |
| 0 μg/mouse + 10 μg/mouse | 1 | Non-specific Treg |
| 0 μg/mouse + 10 μg/mouse | 0 | Spleen cells |

TABLE 11

Experimental groups.

| Groups | Anti-IL-10 + Anti-CD40L | Anti-body isotype | Specific Treg | Non-specific Treg | Specific Tcon | Spleen cells | In-activated RSV |
|---|---|---|---|---|---|---|---|
| 1 | + | − | + | − | − | + | + |
| 2 | − | + | + | − | − | + | + |
| 3 | − | + | − | + | − | + | + |
| 4 | − | + | − | − | + | + | + |

Figure 8A:
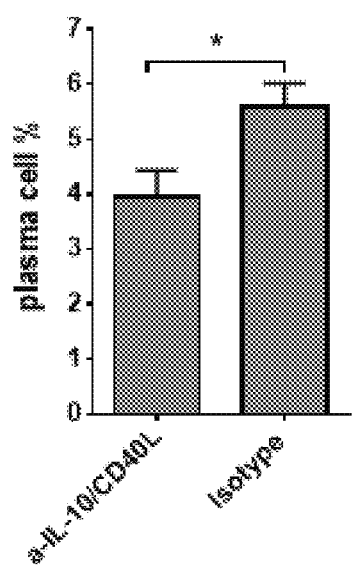
Figure 8B:
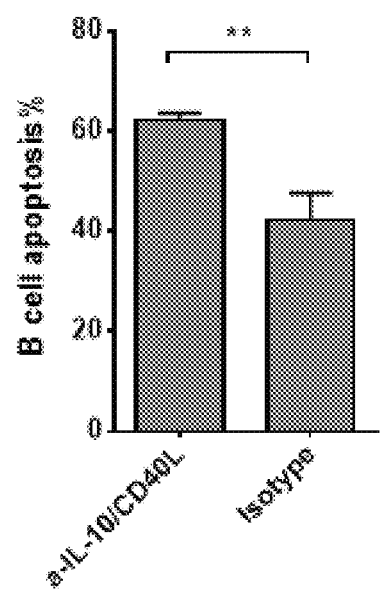

Results: As shown in FIGS. 8A and 8B, G+CsA induced Treg promoted the differentiation of plasma cells and helped maintain a low level of B cell apoptosis, which was inhibited by adding anti-CD40L and anti-IL10. Non-specific Treg cells or specific conventional T cells co-culturing showed no such phenomenon.

Conclusions: G+CsA induced Treg cells rather than conventional T cells promoted the differentiation of plasma cells and prohibited B cells apoptosis. The assistant role of G+CsA induced Treg on B cells involves in CD40L and IL-10.

Example 8. CsA+Recombinant G Protein Vaccination Provided Protection for Neonate Mice A. Recombinant G Protein+CsA Vaccination Protects Neonate Mice from RSV Infection Materials: Parental BALB/c mice were purchased from Beijing Huafukang Bioscience Co. Inc (Beijing, China), and neonates were inbred obtained from parental animal. Breeding cages were checked daily for new birth, and the day of birth was recorded as day 0.

Methods: Groups were set according to Table 12. FI-RSV as formalin inactivated RSV, was set as control. The 5-day-old mice were immunized intramuscularly at day 0, 14. At day 28, mice were infected with RSV. At day 32, mice were euthanized for samples collection. Serum samples were obtained for ELISA analysis of anti-G IgG and RSV neutralizing antibody. Lung tissues were collected for RSV viral load detection by RT-PCR. Histopathological changes of lung tissues including inflammatory cell infiltration were evaluated with hematoxylin and eosin (H&E) and Periodic Acid-Schiff (PAS) staining.

TABLE 12

Experimental groups

| Groups | Vaccination substance | RSV infection |
|---|---|---|
| 1 | — | — |
| 2 | PBS | 1 |
| 3 | CsA 10 μg/mouse | 1 |
| 4 | recombinant G Protein 10 μg/mouse | 1 |
| 5 | CsA 10 μg/mouse + recombinant G Protein 10 μg/mouse | 1 |
| 6 | FI-RSV | 1 |

Figure 9A:
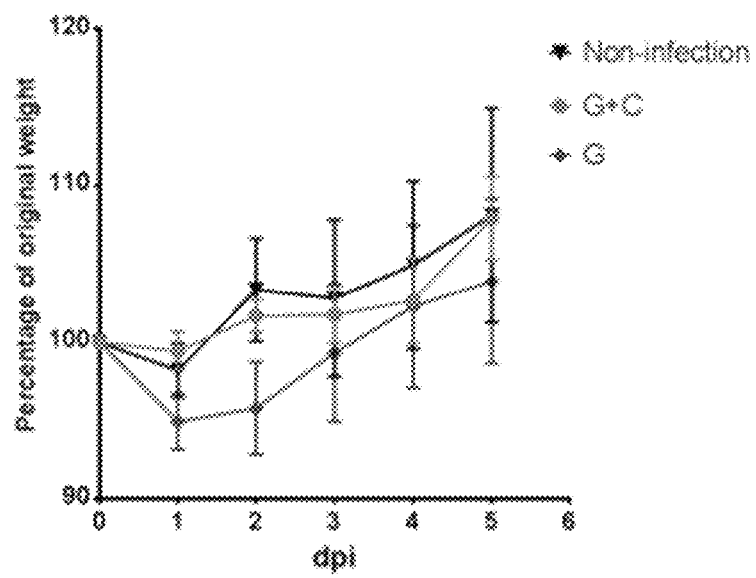
Figure 9B:
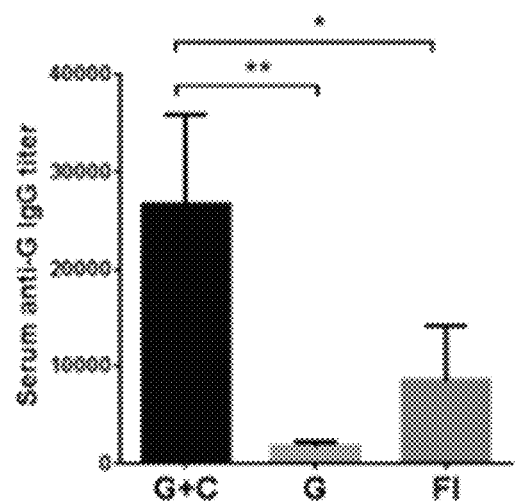
Figure 9C:
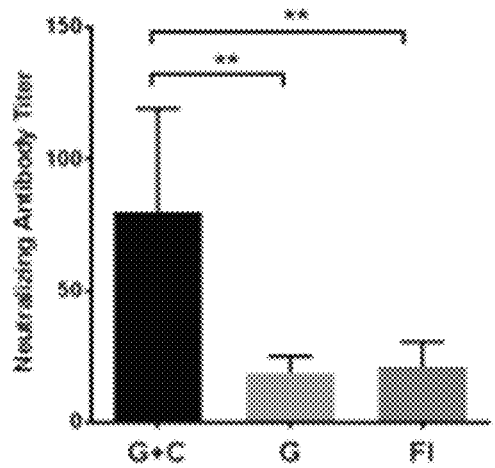

Results: As shown in FIG. 9A, there was no difference in weight changes between recombinant RSV G protein+CsA vaccinated mice and uninfected mice, both of which were increasing daily. In mice vaccinated with recombinant G protein only, ascending trends of weight were significantly slower than mice vaccinated with recombinant G protein+CsA. In the serum of mice vaccinated with recombinant G protein+CsA, levels of anti-G IgG (FIG. 9B) and RSV neutralizing antibody (FIG. 9C) were both significantly higher than the mice vaccinated with recombinant G protein and mice vaccinated with FI-RSV. HE staining revealed that immunization with recombinant G protein+CsA followed by challenge or non-infection resulted in little lymphocytes infiltration. While the other groups manifested lymphocytes infiltration to different extents. According to the PAS stained slides, no distinct mucin accumulation was observed in mice vaccinated recombinant G protein+CsA and mice uninfected with RSV, and in other groups, all mice were showed different levels of mucin accumulation in pulmonary bronchus. All lung tissue slides showed recombinant G protein+CsA vaccination inhibited pulmonary inflammation after RSV infection in neonate mice, compared with mice vaccinated with recombinant G protein only and mice vaccinated with FI-RSV showing severe inflammation.

Conclusion: recombinant G protein+CsA vaccination protects neonate mice from RSV infection and prevents inflammation enhancement phenomenon after immunization.

B. Numbers and Functions of Recombinant G Protein+CsA Induced Treg and GC B Cell Materials: Parental BALB/c mice were purchased from Beijing Huafukang Bioscience Co. Inc (Beijing, China), and neonates were inbred obtained from parental animal. Breeding cages were checked daily for new birth, and the day of birth was recorded as day 0.

Methods:
1) Mice of 5-day-old were immunized with recombinant G protein+CsA or recombinant G protein only at day 0, 14. At day 17, 21, 24, 28, spleen and lymph nodes were isolated for detection of ICOS expressed on Treg cells.
2) Mice were immunized with recombinant G protein+CsA or recombinant G protein only at day 0. At day 7, spleens were isolated for detection of CD80, CD86 and MHC-II expression on B cells and numbers of B cells.

Figure 9D:
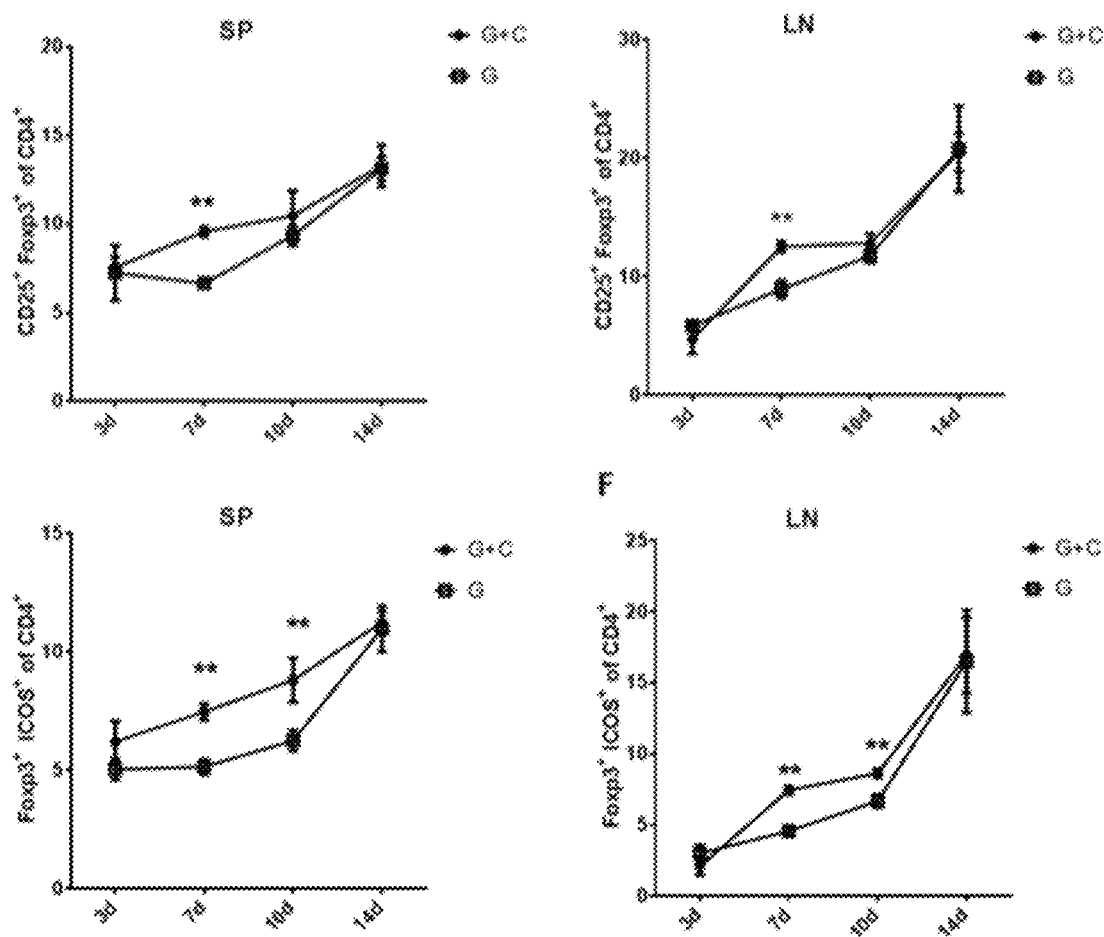
Figure 9E:
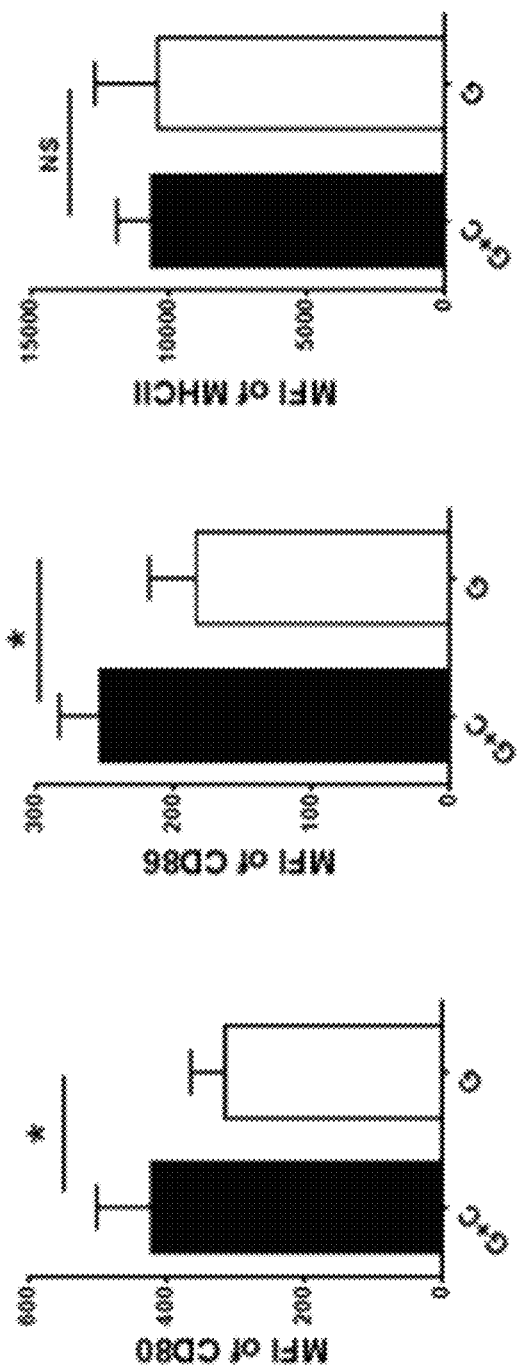

Results:
1) As shown in FIG. 9D, at day 7 (upper panels) and day 10 (lower panels), numbers of Treg cells in mice vaccinated with recombinant G protein+CsA were significantly higher than in mice vaccinated with recombinant G protein only. At day 21 and day 24, ICOS expressed on Treg cells from mice vaccinated with recombinant G protein+CsA was significantly higher than Treg cells from mice vaccinated with recombinant G protein only, but no difference was observed at day 28 between both groups.
2) At day 7 after the first immunization, GC B cells were significantly higher in mice vaccinated with recombinant G protein+CsA compared with mice vaccinated with recombinant G protein only, indicating CsA as an immune regulator to recombinant G protein vaccination promotes the generation of GC B cells. Additionally, CD80, CD86 were significantly higher expressed on spleen B cells in mice vaccinated with recombinant G protein+CsA (FIG. 9E, left and middle panels), while no difference in MHC-II expression (FIG. 9E, right panel).

Conclusions:
1) Vaccination with recombinant G protein+CsA induced a group of Treg cells rapidly in neonate mice, which was significant in the early period. With the growth of neonate mice, the difference of the numbers of Treg cells was covered by the development of immune organs and the increase of immune cells. Vaccine induced Tregs can be activated in the very early of the development stage, while other sources of Tregs join in to restrain the vaccination induced inflammation afterwards, which also express ICOS, covering up the functions of vaccine induced Treg cells. Vaccination with recombinant G protein+CsA induces a group of Treg cells in early period of neonate mice, functioning rapidly after activation by antigen in the vaccine.

2) Increased expression of CD80 and CD86 proved the activation of B cells in the spleen, signals of reaction on T cells and interactions between T cells and B cells. This indicated that CsA, as an adjuvant to the recombinant G protein in the vaccine, promoted the B cells bio-functions, mediated by interactions between T cells and B cells. No difference observed in expression of MHC-II indicated that the vaccination has no influence on B cells antigen presenting ability.

C. Cytokines Detection of Recombinant G Protein+CsA Induced Treg

Materials: Parental BALB/c mice were purchased from Beijing Huafukang Bioscience Co. Inc (Beijing, China), and neonates were inbred obtained from parental animal. Breeding cages were checked daily for new birth, and the day of birth was recorded as day 0.

Methods: At day 0, 14, mice were vaccinated with recombinant G protein+CsA or recombinant G protein only. At day 28, mice were infected with RSV. At day 32, all mice were euthanized for spleen isolation. Separated spleen cells were co-cultured with purified G protein for IL-10 in CD4+ cells detection. Experimental groups are shown in Table 13.

TABLE 13

Experimental groups

| Groups | Spleen cells recombinant G protein + CsA | Spleen cells recombinant G Protein | Purified recombinant G protein |
|---|---|---|---|
| 1 | + | − | + |
| 2 | − | + | + |

Figure 9F:
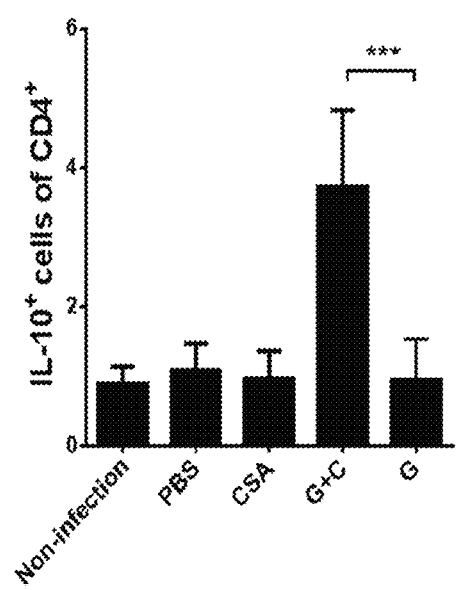
Figure 10A:
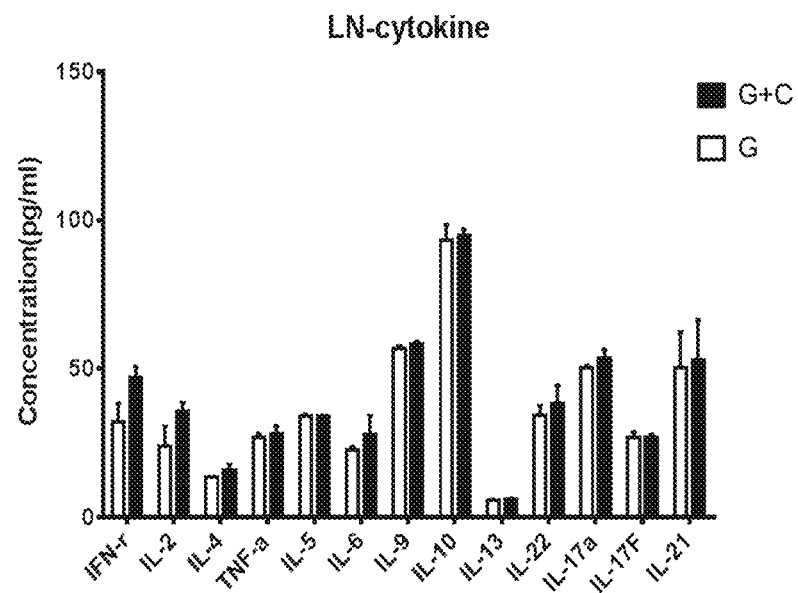
Figure 10B:
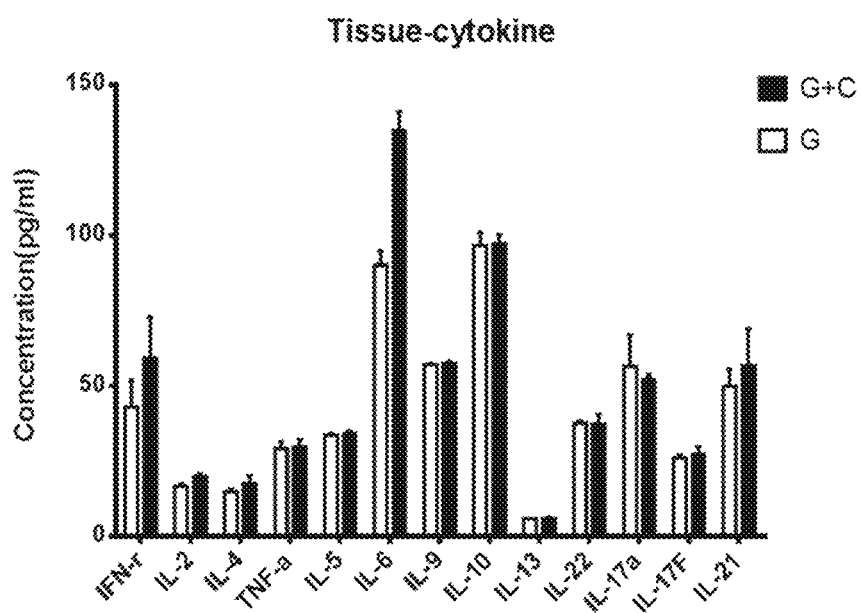
Figure 10C:
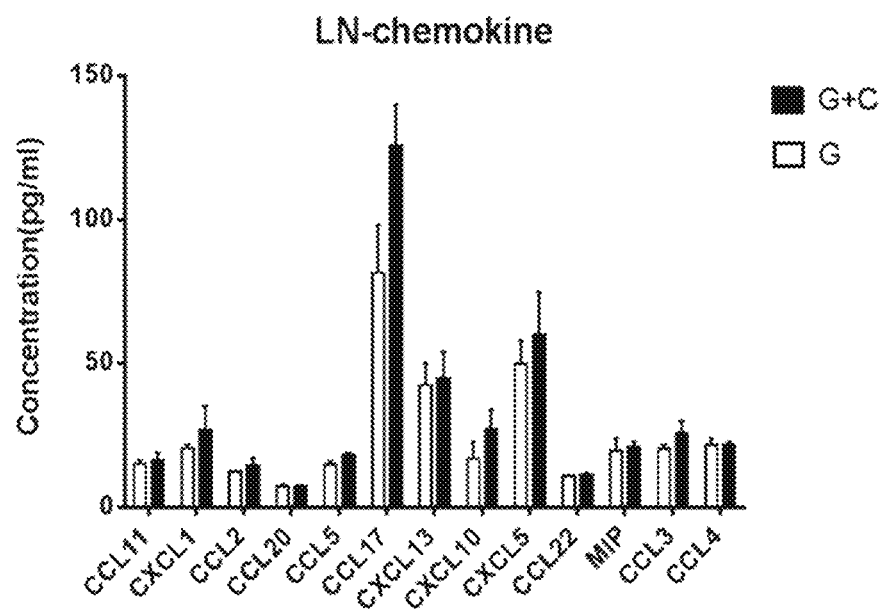
Figure 10D:
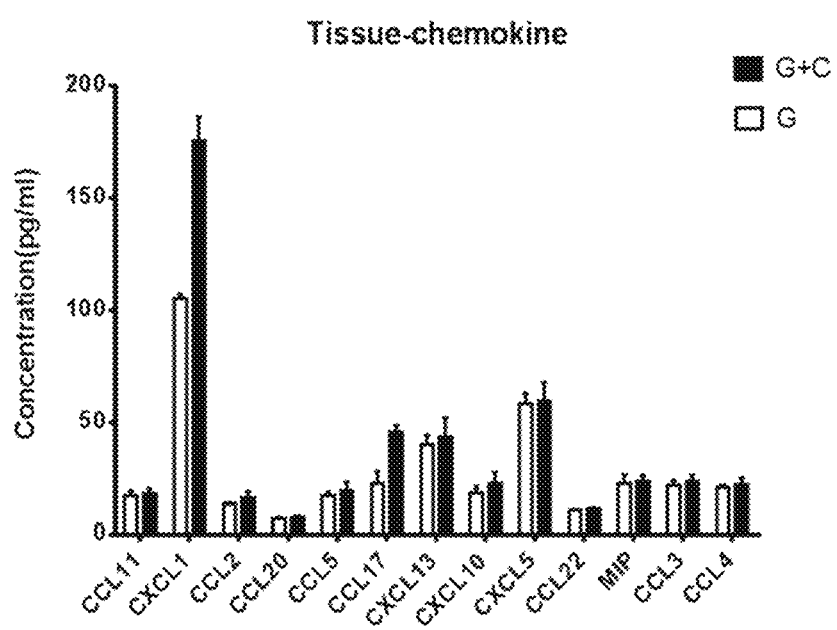

Results: IL-10 highly expressed CD4+ T cells were only detected in mice vaccinated with recombinant G protein+CsA. FIG. 9F.

Conclusions: IL-10 specifically secreted CD4+ T cells exist in spleen of mice vaccinated with recombinant G protein+CsA, rather than mice vaccinated with recombinant G protein only. Alike adult mice, vaccine induced Treg cells functioned by IL-10 secretion.

D. Cytokines Alteration in Immunizing Situ and Lymph Nodes Nearby

Materials: Parental BALB/c mice were purchased from Beijing Huafukang Bioscience Co. Inc (Beijing, China), and neonates were inbred obtained from parental animal. Breeding cages were checked daily for new birth, and the day of birth was recorded as day 0.

Methods: Mice were immunized with recombinant G protein+CsA or recombinant G protein only, then were all euthanized 3 hours afterwards for cytokines detection in immunizing situ and lymph nodes nearby. Cytokines, including IFN-r, IL-2, IL-4, TNF-α, IL-5, IL-6, IL-9, IL-10, IL-13, IL-22, IL-17a, IL-17F, IL-21 and chemokines, including CCL11, CXCL1, CCL2, CCL20, CCL5, CCL17, CXCL13, CXCL10, CXCL5, CCL22, MIP, CCL3, CCL4, were detected.

Results: IL-6, CCL17 and CXCL1 were significantly higher in immunizing tissue from mice vaccinated with recombinant G protein+CsA compared with mice vaccinated with recombinant G protein only, and no other difference was observed. In lymph nodes near the vaccination site, CCL17 were detected significantly higher in mice vaccinated with recombinant G protein+CsA. FIGS. 10A-10D.

Conclusions: IL-6 is an important inflammatory cytokine. CXCL1, a chemokine belonging to the CXC family, is mainly secreted by macrophage, neutrophils and epithelial cells. CCL17 belongs to CC family, mainly functioning as chemokines.

Example 9. Dosage Optimization of RSV G Proteins in Vaccination

1. Immunization

Materials: Female 6- to 8-wk-old BALB/c mice were purchased from Beijing Huafukang Bioscience Co. Inc (Beijing, China). All mice were kept according to the animal welfare guidelines for experimental animals.

The mice were randomly divided into groups with five mice every group. These mice were immunized subcutaneously at day 0 and day 14 with recombinant G protein+CsA, recombinant G protein or PBS 100 µl per mouse. To explore the optimal CsA and recombinant G protein immunization dosage, RSV vaccine groups included 10 µg CsA+10 µg recombinant G protein, 10 µg CsA+3.33 µg recombinant G protein, 10 µg CsA+1.11 µg recombinant G protein, 10 µg CsA+0.37 µg recombinant G protein, 10 µg recombinant G protein, 3.33 µg recombinant G protein, 1.11 µg recombinant G protein and 0.37 µg recombinant G protein, shown as the Table 14 below.

TABLE 14

Vaccine dosage of CsA and recombinant G protein

| Groups | CsA (µg per mouse) | recombinant G protein (µg per mouse) |
|---|---|---|
| PBS | 0 | 0 |
| G protein | 0 | 10 |
|  | 0 | 3.33 |
|  | 0 | 1.11 |
|  | 0 | 0.37 |
| recombinant G protein + CsA | 10 | 10 |
|  | 10 | 3.33 |
|  | 10 | 1.11 |
|  | 10 | 0.37 |

2. Assay of Antibodies

The peripheral blood samples were obtained on days 0, 14 and 28 after the first immunization for serum antibodies level detection. Protocols were shown below:

1) Serum separation

The blood samples were incubated two hours at 37° C. to clot, and then centrifuged 3000 rpm 10 min to separate serum for −80° C. storage.

2) Anti-G Abs detection

A. The plates of 96-well were coated with recombinant G protein 2 µg/ml 100 µl per well at 37° C. for 2h or at 4° C. overnight.

B. The plates were washed three times with PBST, and blocked with 5% fat-free milk 37° C. for an hour.

C. Serum samples were serially diluted (two-fold) with 2% fat-free milk, and added 100 µl per well into plates washed three times with PBST.

D. After incubation for one hour 37° C., the plates were washed three times with PBST. Bound Abs were then captured with HRP-conjugated goat anti-mouse IgG 100 µl per well, which was diluted 4000-fold with 2% fat-free milk previously. The plates were washed six times with PBST after incubation 37° C. for an hour.

E. The enzymatic reaction was conducted with 100 µl TMB substrate solution 37° C. for 15 min, and then stopped with 0.2 mol/L sulfuric acid 100 µl. ODs were read at 450/620 nm by an ELISA plate reader. The antibody titer was measured as the serum dilution whose ODs were two-fold more than the negative control.

Figure 11A:
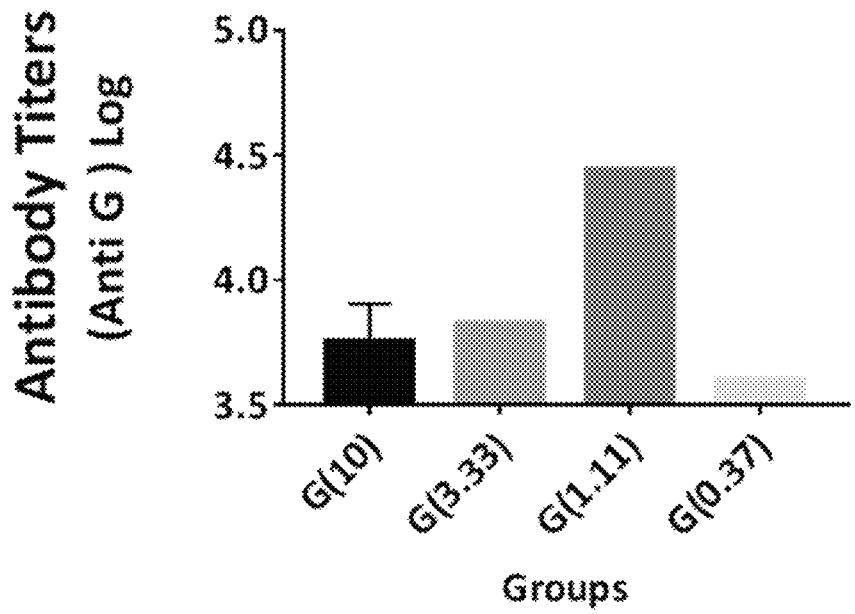
Figure 11B:
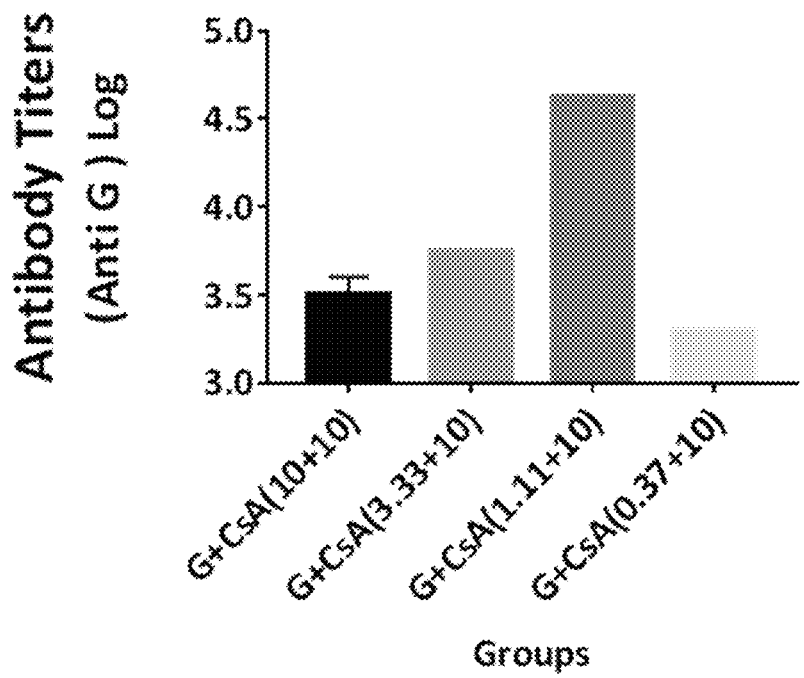

Results shown in FIGS. 11A-11B suggested that immunization with different dosages of recombinant G protein only or with CsA stimulated anti-G IgG Abs to some extent. Though the antibody level stimulated with different ratios of recombinant G protein to CsA existed with variances, vaccination with 1.11 µg recombinant G protein+10 µg CsA or 1.11 µg recombinant G protein promoted higher antibody titers than other groups (FIGS. 11A-11B). Serum of PBS injected mice had very low-level anti-G IgG Abs, indicating no specific antibody stimulation effect.

In summary, the RSV vaccine induced high-level humoral immune responses dependents the dosage of RSV vaccine.

Example 10. Screening for Formulation and Adjuvants for Preparation of Immune Compositions Against RSV Infection 1. Immunization Materials: Female 6-8-wks-old BALB/c mice are purchased from Beijing Huafukang Bioscience Co. Inc (Beijing, China). All mice are kept according to the animal welfare guidelines for experimental animals.

Vaccine formulation and groups are shown in Table 15 below (Dex for dexamethasone, Rap for rapamycin). These mice are immunized subcutaneously at day 0 and day 14, 200 µl injection volume per mouse.

TABLE 15

Recombinant G protein and immuno modulator

| Groups | immune modulator | immuno modulator dosage (µg per mouse) | recombinant G protein (µg per mouse) |
|---|---|---|---|
| PBS | 0 | 0 | 0 |
| recombinant G protein | | 0 | 10 |
| CsA + recombinant G protein | CsA | 1 | 10 |
| | | 10 | 10 |
| | | 100 | 10 |
| Dex + recombinant G protein | Dex | 1 | 10 |
| | | 10 | 10 |
| | | 100 | 10 |
| FK506 + recombinant G protein | FK506 | 1 | 10 |
| | | 10 | 10 |
| | | 100 | 10 |
| Rap + recombinant G protein | Rap | 1 | 10 |
| | | 10 | 10 |
| | | 100 | 10 |
| CsA | CsA | 1 | 0 |
| | | 10 | 0 |
| | | 100 | 0 |
| Dex | Dex | 1 | 0 |
| | | 10 | 0 |
| | | 100 | 0 |
| FK506 | FK506 | 1 | 0 |
| | | 10 | 0 |
| | | 100 | 0 |
| Rap | Rap | 1 | 0 |
| | | 10 | 0 |
| | | 100 | 0 |

2. Assay of Antibodies

The peripheral blood samples are obtained on days 0, 14 and 28 after the first immunization for serum antibodies level detection following the below protocols.

1) Serum separation

The blood samples are incubated two hours at 37° C. to clot, and then centrifuged 3000 rpm 10 min to separate serum for −80° C. storage.

2) Anti-G Abs detection

A. The plates of 96-well are coated with recombinant G protein 2 µg/ml 100 µl per well at 37° C. for 2h or at 4° C. overnight.

B. The plates are washed three times with PBST, and blocked with 5% fat-free milk 37° C. for an hour.

C. Serum samples are serially diluted (two-fold) with 2% fat-free milk, and added 100 µl per well into plates washed three times with PBST.

D. After incubation for one hour 37° C., the plates are washed three times with PBST. Bound Abs are then captured with HRP-conjugated goat anti-mouse IgG 100 µl per well, which is diluted 4000-fold with 2% fat-free milk previously. The plates are washed six times with PBST after incubation 37° C. for an hour.

E. The enzymatic reaction is conducted with 100 µl TMB substrate solution 37° C. for 15 min, and then stopped with 0.2 mol/L sulfuric acid. ODs are read at 450/620 nm by an ELISA plate reader. The antibody titer is measured as the dilution fold, in which ODs are more than two-fold than the negative controls.

3. Neutralizing Antibody Assay

A. The serum samples are incubated 56° C. for 30 min to inactivate complements. The serially diluted (two-fold) serum in MEM medium supplemented with 2% FBS are added 75 µl each well of cell culture 96-well plates.

B. RSV virus suspended at $10^4$ $TCID_{50}$ are added 25 µl each well and mixed with serum thoroughly for 4° C. incubation 2h. Then $1.5 \times 10^4$ Hep-2 cells in 100 µl MEM medium supplemented with 5% FBS are added to each well and incubated for 72h in a 5% CO2 incubator at 37° C.

C. Plates are then washed three times with PBST and fixed with 80% cold acetone in PBS for 4° C. incubation 15 min. Then the liquid is dropped and the plates are dried at room temperature.

D. The plates are blocked with 5% fat-free milk in PBST by 37° C. incubation one hour followed by three washings with PBST.

E. Goat anti-RSV Ab diluted 5000-fold with 3% fat-free milk in PBST is added 100 µl each well and incubated for an hour at 37° C.

F. After three washings, bovine anti-goat IgG-HRP diluted 2000-fold with 3% fat-free milk in PBST is added 100 µl each well and incubated for an hour at 37° C.

G. After three washings, the enzymatic reaction is developed with 100 µl TMB substrate solution 37° C. for 15 min.

H. The enzymatic reaction is stopped with 0.2 mol/L sulfuric acid 504

I. ODs were read at 450/620 nm by an ELISA plate reader, and ODs were read at 450/620 nm by an ELISA plate reader. Neutralizing Ab titers are extrapolated by the serum dilution that resulted in 50% reduction of RSV activity.

4. DTH Assay

These mice are injected s.c. with recombinant G protein in the left footpad and PBS in the right footpad 7 days after the primary vaccination. The footpad thickness is measured with the caliper three times in the same site. The average of the triplicates is the final size. DTH footpad swelling=left footpad thickness/mm−right footpad thickness/mm.

5. Lung Index Detection Post RSV Challenge

After 7 days post the final vaccination, these mice are infected with RSV virus, 6×10$^5$ TCID50 per mouse. The mice are sacrificed 5 days later. Lung index=lung weight/body weight 6. Changes of Body Weight Post RSV Challenge After 7 days post the final vaccination, these mice are infected with RSV virus, 6×10$^5$ TCID50 per mouse. The mice are weighed every day for 5 days.

7. Histopathology

After 7 days post the final vaccination, these mice are infected with RSV virus, 6×10$^5$ TCID50 per mouse. The mice are sacrificed 5 days later to collect lung tissues for H&E histopathological evaluations, noninfected naïve mice as controls. The protocol as follow: lung tissues are fixed with 10% formalin for 3-7 days followed by dehydration, paraffin embedding, slicing, hematoxylin and eosin staining and mounting. The slides are observed with microscope and graded on the basis of a cumulative score from 5 categories: (1) peribronchiolar and bronchial infiltrates, (2) bronchiolar and bronchial luminal exudates, (3) perivascular infiltrates, (4) the number of monocytes, and (5) parenchymal pneumonia. Scoring 4 represents severe, 3 minor severe, 2 moderate and 1 mild. See "Respiratory Syncytial Virus Induces Pneumonia, Cytokine Response, Airway Obstruction, and Chronic Inflammatory Infiltrates Associated with Long-Term Airway Hyperresponsiveness in Mice".

8. Treg Cells Detection

These mice are immunized subcutaneously with vaccines shown above at day 0 and day 14. The PBS injection volume is 100 µl and the FI-RSV group is immunized with 50 µl 5×10$^7$ TCID50 inactivated RSV virus. The iTreg in spleen, lymph node and bronchoalveolar lavage (BAL) are detected with flow cytometry.

After 7 days post the final vaccination, these mice are infected with RSV virus, 6×10$^5$ TCID50 per mouse. The mice are anaesthetized with 1% phenobarbital sodium solution (60 µg/kg) at 4 days post RSV infection. BAL are obtained by infusing 1 mL of PBS containing 0.2% FBS through a needle into the lungs via the trachea, followed by aspiration of this fluid into a syringe. BAL are centrifuged to collect cells. The hilar lymph nodes and spleen are obtained and grinded to prepare single cell suspension. The single suspension is stained as protocol Foxp3/Transcription Factor Staining Buffer Set and followed by flow cytometry assay.

Example 11. Screening for Suitable Immune Regulators and Excipients for Making Immune Compositions 1. Tested Cells JAWSII cells (mouse bone marrow cells) were recovery from liquid nitrogen and put into a water bath at 37° C. The cells were washed twice with the MEM media. The recovered cells were cultured in 10 mL cMEM (MEM+20% FBS+5 ng/mL rmGM-CSF) for 5-7 days. The cells were ready for use after 2 passages.

2. Cells Stimulation

Figure 13:
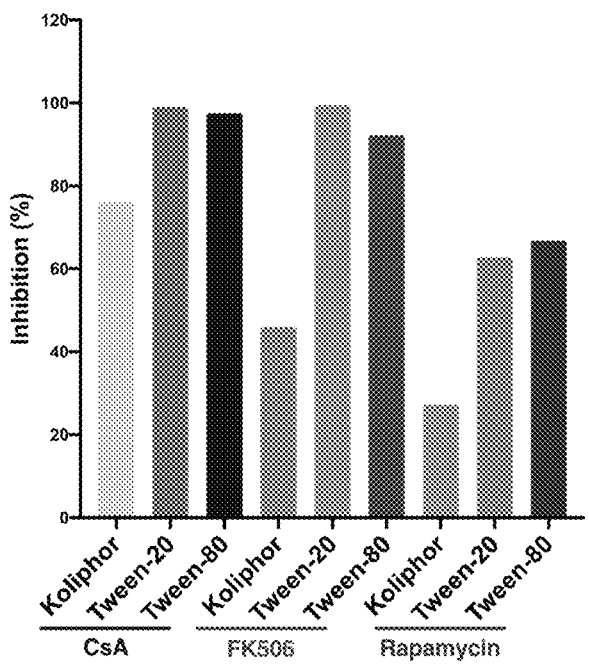
FIG. 13 is a chart showing immune response of various combinations of immune regulators and non-ionic surfactants as indicated.

The JAWSII cells were cultured in cMEM for 24 hours at 5×10$^5$ cells/well in a 24-well plate for 24 hours in the presence of immune activated stimulators (LPS+Alum, as the control) and various immune regulators, including CsA, FK506 and rapamycin, either alone or in combination with a surfactant selected from Polyethylene glycol (15)-hydroxystearate, polysorbate 20 (Tween® 20), or polysorbate 80 (Tween® 80). Further, the cells were incubated in the presence of LPS+Alum (as a positive control), medium (as a blank control) and CsA, and 5 various excipients as indicated in FIG. 13. The cell supernatant was collected for further analysis.

3. Immune Active Biomarker Measurement

Each supernatant noted above was centrifuged under 12000 rpm at 4° C. for 5 minutes. The level of IL-1β (an immune active biomarker) was measured following the ELISA procedure provided below.

4. ELISA Procedure

1. Prepare all reagents and working standards.

2. Remove excess microplate strips from the plate frame, return them to the foil pouch containing the desiccant pack, and reseal.

3. Add 300 µl Wash Buffer (lx) per well, and allow the Wash Buffer to sit in the wells for about 30 seconds before aspiration. Soaking is highly recommended to obtain a good test performance! Empty wells and tap microwell strips on absorbent pad or paper towel to remove excess Wash Buffer. Use the microwell strips immediately after washing. Do not allow wells to dry.

4. Add 100 µl of 2-fold diluted Standard in duplicate and 100 µl of Standard Diluent to Blank well in duplicate.

5. Add 80 µl of Assay Buffer (lx) and 20 µl sample to the sample well.

6. Add 50 µl of diluted Detect Antibody to each well. Ensure reagent addition in step 4, 5 and 6 is uninterrupted and completed within 15 minutes.

7. Cover with an adhesive strip. Incubate at room temperature (18 to 25° C.) for 1.5 hours on a microplate shaker set at 300 rpm.

8. Aspirate each well and wash, repeating the process five times for a total six washes. Wash by filling each well with 300 µl Wash Buffer (1×). Complete removal of liquid at each step is essential to good performance. After the last wash, remove any remaining Wash Buffer by aspirating or decanting. Invert the plate and blot it against clean paper towels.

9. Add 100 µl of diluted Streptavidin-HRP to each well.

10. Cover with a new adhesive strip. Incubate at room temperature (18 to 25° C.) for 30 minutes on a microplate shaker set at 300 rpm.

11. Repeat aspiration/wash as in step 8.

12. Add 100 µl of Substrate Solution to each well. Incubate for 5-30 minutes at room temperature. Protect from light.

13. Add 100 µl of Stop Solution to each well. The color in the well should change from blue to yellow. If the color in the well is green or if the color change does not appear uniform, gently tap the plate to ensure thorough mixing.

14. Determine the optical density within 30 minutes, using microplate reader set to 450 nm/620 nm, subtract readings at 620 nm from the readings at 450 nm.

15. Calculate the IL-1β concentration of tested subject by standard curve. Inhibition percentage (%) was calculated as the percentage of the reduction of IL-1β level of each tested sample as compared with the positive control (LPS+Alum) and the blank control.

Figure 12:
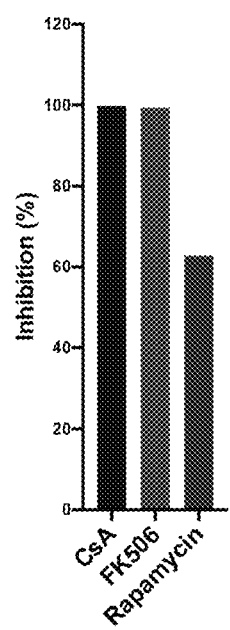
FIG. 12 is a chart showing the immune suppression effects of CsA, FK506 and rapamycin.

Results:

As shown in FIG. 12, CsA and FK506 showed around 100% inhibition (immune suppression), while rapamycin showed around 60% inhibition.

FIG. 13 shows the inhibitory activity of CsA, FK506, and rapamycin in combination of one of the listed surfactants. All combinations showed certain levels of inhibition. CsA or FK506 in combination with polysorbate 20 or polysorbate 80 showed better inhibitory activity relative to compositions containing Koliphor® HS 15 (Polyethylene glycol (15)-hydroxystearate) as the surfactant or rapamycin as the immune regulator.

Figure 14:
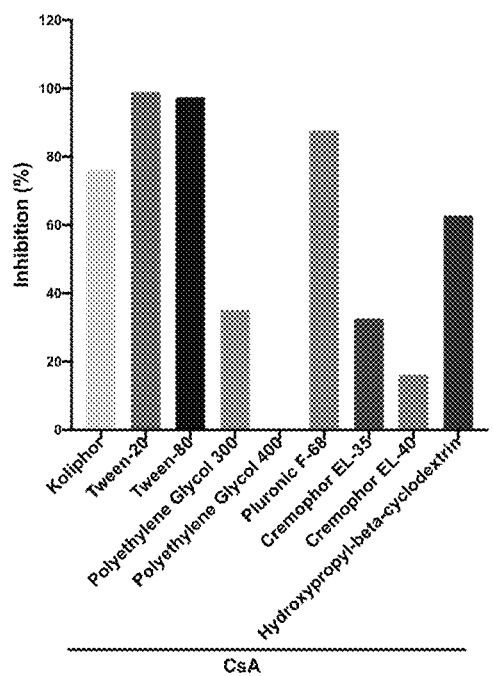
FIG. 14 is a chart showing immune response of CsA in combination with various non-ionic surfactants as indicated.

The inhibitory activities of CsA in combination with different surfactants are shown in FIG. 14. CsA in combination with Koliphor® HS 15 (polyethylene glycol (15)-hydroxystearate), Tween® 20 (polysorbate 20), Tween® 80 (polysorbate 80), Pluronic® F-68 (poloxamer 188, a polyoxyethylene-polyoxypropylene block copolymer), or hydroxypropyl-beta-cyclodextrin demonstrated better activity than CsA in combination with the other tested surfactants.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An immune composition, comprising (i) a modified respiratory syncytial virus (RSV) G polypeptide or a nucleic acid encoding the modified RSV G polypeptide, and (ii) an immune regulator;
   wherein the modified RSV polypeptide lacks a transmembrane domain as compared with the wild-type counterpart,
   wherein the modified RSV G polypeptide comprises the amino acid sequence of any one of SEQ ID NOs:1-4;
   wherein the immune regulator is cyclosporin A; and
   wherein the immune composition further comprises a non-ionic surfactant, which comprises polyethylene glycol (15)-hydroxystearate.

2. The immune composition of claim 1, wherein the modified RSV G polypeptide comprises the amino acid sequence of SEQ ID NO: 4.

3. The immune composition of claim 1, which comprises the modified RSV G polypeptide.

4. The immune composition of claim 3, wherein the modified RSV G polypeptide consists of the amino acid sequence of any one of SEQ ID NOs:1-4.

5. The immune composition of claim 1, which comprises a nucleic acid encoding the modified RSV G polypeptide.

6. The immune composition of claim 5, wherein the nucleic acid comprises a nucleotide sequence at least 80% identical to any one of SEQ ID NOs. 5-8.

7. The immune composition of claim 6, wherein the nucleic acid comprises the nucleotide sequence of any one of SEQ ID NOs: 5-8.

8. The immune composition of claim 1, wherein immune composition comprises the modified RSV G polypeptide; and wherein the cyclosporine compound and the modified RSV G polypeptide are at a ratio of 10:1 to 1:10 by weight in the immune composition.

9. The immune composition of claim 8, wherein the immune composition is a dosage form comprising about 10-50 mg of the modified RSV G polypeptide and about 10-50 mg of the cyclosporine A.

10. The immune composition of claim 8, which comprises (a) a respiratory syncytial virus (RSV) G polypeptide comprising the amino acid sequence of SEQ ID NO:4, (b)
   polyethylene glycol (15)-hydroxystearate; and
   cyclosporine A.

11. A method for enhancing immune responses against a respiratory syncytial virus (RSV), the method comprising administering to a subject in need thereof an effective amount of an immune composition set forth in claim 1.

12. A kit for enhancing immune responses against a respiratory syncytial virus (RSV), the kit comprising:
   (a) a first solution comprising a respiratory syncytial virus (RSV) G protein, an immunogenic fragment thereof, or a nucleic acid encoding such; and
   (b) a second solution comprising an immune regulator dissolved in a non-ionic surfactant solvent, wherein the immune regulator is cyclosporin A; and wherein the non-ionic surfactant comprises polyethylene glycol (15)-12-hydroxystearate.

* * * * *